United States Patent
Heidebrecht, Jr. et al.

(10) Patent No.: US 8,461,189 B2
(45) Date of Patent: *Jun. 11, 2013

(54) PYRIDYL DERIVATIVES AS HISTONE DEACETYLASE INHIBITORS

(75) Inventors: Richard W. Heidebrecht, Jr., Brookline, MA (US); Thomas A. Miller, Brookline, MA (US); Matthew G. Stanton, Medfield, MA (US); David J. Witter, Norfolk, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 358 days.

This patent is subject to a terminal disclaimer.

(21) Appl. No.: 12/666,415

(22) PCT Filed: Jun. 24, 2008

(86) PCT No.: PCT/US2008/007853
§ 371 (c)(1),
(2), (4) Date: Dec. 23, 2009

(87) PCT Pub. No.: WO2009/005638
PCT Pub. Date: Jan. 8, 2009

(65) Prior Publication Data
US 2010/0324092 A1    Dec. 23, 2010

Related U.S. Application Data

(60) Provisional application No. 60/937,411, filed on Jun. 27, 2007, provisional application No. 60/999,171, filed on Oct. 16, 2007.

(51) Int. Cl.
A01N 43/40    (2006.01)
A01N 47/10    (2006.01)
A61K 31/44    (2006.01)
C07D 213/55   (2006.01)

(52) U.S. Cl.
USPC ........... 514/357; 514/487; 546/305; 546/265; 546/247; 546/146

(58) Field of Classification Search
USPC ................... 546/308, 265; 514/357, 487
See application file for complete search history.

(56) References Cited

U.S. PATENT DOCUMENTS

| | | | |
|---|---|---|---|
| 4,670,438 A | 6/1987 | Austel et al. | |
| 4,766,130 A | 8/1988 | Austel et al. | |
| 5,369,108 A | 11/1994 | Breslow et al. | |
| 5,700,811 A | 12/1997 | Breslow et al. | |
| 5,932,616 A | 8/1999 | Breslow et al. | |
| 6,087,367 A | 7/2000 | Breslow et al. | |
| 6,174,905 B1 | 1/2001 | Suzuki et al. | |
| 6,407,131 B1 | 6/2002 | Quada, Jr. et al. | |
| 6,506,783 B1 | 1/2003 | Camden et al. | |
| 6,511,990 B1 | 1/2003 | Breslow et al. | |
| 6,710,065 B1 | 3/2004 | Camden et al. | |
| 6,794,392 B1 | 9/2004 | Suzuki et al. | |
| 6,864,275 B1 | 3/2005 | Camden et al. | |
| 6,984,654 B2 | 1/2006 | Camden et al. | |
| 7,169,801 B2 | 1/2007 | Bressi et al. | |
| 7,834,034 B2 | 11/2010 | Mampreian et al. | |
| 7,868,204 B2 | 1/2011 | Delorme et al. | |
| 7,981,874 B2 * | 7/2011 | Close et al. | 514/110 |
| 8,026,260 B2 | 9/2011 | Close et al. | |
| 8,119,685 B2 | 2/2012 | Heidebrecht et al. | |
| 2003/0139404 A1 | 7/2003 | Haag et al. | |
| 2004/0142953 A1 | 7/2004 | Delorme et al. | |
| 2004/0192744 A1 | 9/2004 | Haag et al. | |
| 2005/0288282 A1 | 12/2005 | Delorme et al. | |
| 2006/0293336 A1 | 12/2006 | Sutton et al. | |
| 2009/0062297 A1 | 3/2009 | Heidebrecht et al. | |
| 2009/0069250 A1 | 3/2009 | Grimm et al. | |
| 2009/0105264 A1 | 4/2009 | Hamblett et al. | |
| 2009/0221669 A1 | 9/2009 | Heidebrecht et al. | |
| 2010/0324046 A1 | 12/2010 | Harrington et al. | |

FOREIGN PATENT DOCUMENTS

| | | |
|---|---|---|
| EP | 0974576 | 11/2003 |
| EP | 1369420 | 12/2003 |
| EP | 1378510 | 1/2004 |
| EP | 0847992 | 6/2004 |
| EP | 1541574 | 6/2005 |
| EP | 1547585 | 6/2005 |
| JP | 10152462 | 6/1998 |
| JP | 11269140 | 10/1999 |
| JP | 11269146 | 10/1999 |
| JP | 11302173 | 11/1999 |
| JP | 11335375 | 12/1999 |
| JP | 2002332267 | 11/2002 |

(Continued)

OTHER PUBLICATIONS

Goodman and Gilman 9th Ed (1996) p. 1225-1232, 1269-1271.*

(Continued)

*Primary Examiner* — Shirley V Gembeh
(74) *Attorney, Agent, or Firm* — Li Su; David A. Muthard

(57) ABSTRACT

The present invention relates to a novel class of pyridyl and pyrimidinyl derivatives. The pyridyl and pyrimidinyl compounds can be used to treat cancer. The pyridyl and pyrimidinyl compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the pyridyl and pyrimidinyl derivatives and safe dosing regimens of these pharmaceutical compositions, which are easy to follow, and which result in a therapeutically effective amount of the pyridyl and pyrimidinyl derivatives in vivo.

19 Claims, No Drawings

FOREIGN PATENT DOCUMENTS

| | | |
|---|---|---|
| JP | 2003137866 | 5/2003 |
| WO | WO01/30780 | 5/2001 |
| WO | WO01/38322 | 5/2001 |
| WO | WO02/100819 | 12/2002 |
| WO | WO03/013484 | 2/2003 |
| WO | WO03/024448 | 3/2003 |
| WO | WO03/075929 | 9/2003 |
| WO | WO03/076395 | 9/2003 |
| WO | WO03/076422 | 9/2003 |
| WO | WO03/087057 | 10/2003 |
| WO | WO03/092686 | 11/2003 |
| WO | WO2004006858 | 1/2004 |
| WO | WO2004/035525 | 4/2004 |
| WO | WO2004/058234 | 7/2004 |
| WO | WO2004/069823 | 8/2004 |
| WO | WO2004099170 | 11/2004 |
| WO | WO2005/009971 | 2/2005 |
| WO | WO2005/030704 | 4/2005 |
| WO | WO2005/030705 | 4/2005 |
| WO | WO2005/092899 | 10/2005 |
| WO | WO2006/001958 | 1/2006 |
| WO | WO2006/027346 | 3/2006 |
| WO | WO2006055625 | 5/2006 |
| WO | WO2006067445 | 6/2006 |
| WO | WO2006067446 | 6/2006 |
| WO | 2006115845 A1 | 11/2006 |
| WO | 2007087129 A2 | 8/2007 |
| WO | 2007118137 A1 | 10/2007 |
| WO | 2008010985 A2 | 1/2008 |

OTHER PUBLICATIONS

Sheridan J. Chem Inf. Comput. Sci (2002, 42,103-108).*
Patani et al. (Chem. Rev., 1996, vol. 96, pp. 3147-3176).*
Jaboin, et al., Cancer Research, 62(21), pp. 6108-6115 (2002).
Chen, et al., Chemistry—A European Journal, 10(19), pp. 4790-4797 (2004).
Niwas, et al, Indian Journal of Chemistry, Section B: Organic Chemistry Including Medicinal Chemistry, 24B(7), pp. 754-760 (1985).
Moradei, Oscar M. et al., "Novel Aminophenyl Benzamide-Type Histone Deacetylase Inhibitors with Enhanced Potency and Selectivity", Journal of Medicinal Chemistry, Letters; Page Est: 3.6, pp. A-D. Published on Web 1017/2007.
Witter, David J. et al., Optimization of biaryl Selective HDAC1&2 Inhibitors (SHI-1:2), Bioorganic & Medicinal Chemistry Letters, 18:726-731 (2008).
Notice of Allowance for U.S. Appl. No. 12/224,466; dated Dec. 29, 2011; pp. 1-2.

* cited by examiner

PYRIDYL DERIVATIVES AS HISTONE DEACETYLASE INHIBITORS

PRIORITY CLAIM

This application is a §371 application of PCT/US08/007,853 that was filed on Jun. 24, 2008, which claims priority from the U.S. Provisional Application Nos. 60/937,411 filed on Jun. 27, 2007 and 60/999,171 filed on Oct. 16, 2007.

FIELD OF THE INVENTION

The present invention relates to a novel class of pyridyl and pyrimidinyl derivatives. The pyridyl and pyrimidinyl compounds can be used to treat cancer. The pyridyl and pyrimidinyl compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention can also be useful in the prevention and treatment of TRX-mediated diseases, such as autoimmune, allergic and inflammatory diseases, and in the prevention and/or treatment of diseases of the central nervous system (CNS), such as neurodegenerative diseases.

BACKGROUND OF THE INVENTION

Compounds having a hydroxamic acid moiety have been shown to possess useful biological activities. For example, many peptidyl compounds possessing a hydroxamic acid moiety are known to inhibit matrix metalloproteinases (MMPs), which are a family of zinc endopeptidases. The MMPs play a key role in both physiological and pathological tissue degradation. Therefore, peptidyl compounds that have the ability to inhibit the action of MMPs show utility for the treatment or prophylaxis of conditions involving tissue breakdown and inflammation. Further, compounds having a hydroxamic acid moiety have been shown to inhibit histone deacetylases (HDACs), based at least in part on the zinc binding property of the hydroxamic acid group.

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., Nature, 389: 349-52 (1997)). These effects are thought to occur through changes in the structure of chromatin by altering the affinity of histone proteins for coiled DNA in the nucleosome. There are five types of histones that have been identified. Histones H2A, H2B, H3 and H4 are found in the nucleosome, and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., Nature 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. Application 2003/0235588). Further, these hydroxamic acid derivatives have been identified as useful for treating diseases of the central nervous system (CNS) such as neurodegenerative diseases and for treating brain cancer (See, U.S. Application 2004/0087657).

The inhibition of HDAC by the hydroxamic acid containing compound suberoylanilide hydroxamic acid (SAHA) disclosed in the above referenced U.S. Patents, is thought to occur through direct interaction with the catalytic site of the enzyme as demonstrated by X-ray crystallography studies (Finnin, M. S. et al., Nature 401:188-193 (1999)). The result of HDAC inhibition is not believed to have a generalized effect on the genome, but rather, only affects a small subset of the genome (Van Lint, C. et al., Gene Expression 5:245-53 (1996)). Evidence provided by DNA microarrays using malignant cell lines cultured with a HDAC inhibitor shows that there are a finite (1-2%) number of genes whose products are altered. For example, cells treated in culture with HDAC inhibitors show a consistent induction of the cyclin-dependent kinase inhibitor p21 (Archer, S. Shufen, M. Shei, A., Hodin, R. PNAS 95:6791-96 (1998)). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (Dressel, U. et al., Anticancer Research 20(2A):1017-22 (2000)).

Further, hydroxamic acid derivatives such as SAHA have the ability to induce tumor cell growth arrest, differentiation and/or apoptosis (Richon et al., Proc. Natl. Acad. Sci. USA, 93:5705-5708 (1996)). These compounds are targeted towards mechanisms inherent to the ability of a neoplastic cell to become malignant, as they do not appear to have toxicity in doses effective for inhibition of tumor growth in animals (Cohen, L. A. et al., *Anticancer Research* 19:4999-5006 (1999)).

In view of the wide variety of applications for compounds containing hydroxamic acid moieties, the development of new inhibitors having improved properties, for example, increased potency or increased bioavailability is highly desirable.

SUMMARY OF THE INVENTION

The present invention relates to a novel class of pyridyl and pyrimidinyl derivatives. The pyridyl and pyrimidinyl compounds can be used to treat cancer. The pyridyl and pyrimidinyl compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the pyridyl and pyrimidinyl derivatives, and safe, dosing regimens of these pharmaceutical compositions, which are easy to follow, and which result in a therapeutically effective amount of the pyridyl and pyrimidinyl derivatives in vivo.

It has been unexpectedly discovered that certain pyridyl derivatives show improved activity as histone deacetylase (HDAC) inhibitors and/or attenuated off-target activity.

The present invention thus relates to compounds represented by Formula I and pharmaceutically acceptable salts, solvates and hydrates thereof, as detailed herein.

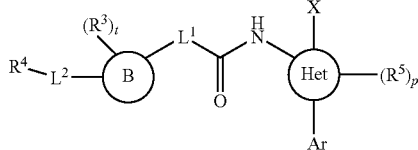
I

DETAILED DESCRIPTION OF THE INVENTION

The present invention relates to a novel class of pyridyl and pyrimidinyl derivatives. In one embodiment, the pyridyl and pyrimidinyl derivatives can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating cancer in a subject. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases.

Compounds

The invention provides a compound represented by the following structural Formula:

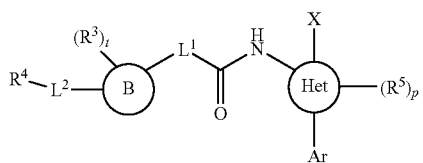
I wherein Ar is aryl or heteroaryl, optionally substituted with halo, methyl, methoxy, halomethyl, amino, hydroxyl, C(O)OCH$_3$ or C(O)NHCH$_3$;

$R^1$ and $R^2$ are independently selected from H, OH, halo, NH$_2$, C$_1$-C$_4$ alkyl, C$_1$-C$_4$ alkenyl, C$_1$-C$_4$ alkynyl, alkoxy, substituted or unsubstituted C$_3$-C$_6$ cycloalkyl, substituted or unsubstituted heteroaryl, substituted or unsubstituted heterocyclic or substituted or unsubstituted aryl;

$R^3$ is independently selected from H, OH, NH$_2$, nitro, CN, amide, carboxyl, C$_1$-C$_7$ alkoxy, C$_1$-C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$ alkyl-C(=O)O—, C$_1$-C$_7$ alkyl-C(=O)—, C$_1$-C$_7$ alkynyl, halo, hydroxyalkoxy, C$_1$-C$_7$ alkyl-NHSO$_2$—, C$_1$-C$_7$ alkyl-SO$_2$NH—, C$_1$-C$_7$ alkylsulfonyl, C$_1$-C$_7$ alkylamino or di(C$_1$-C$_7$)alkylamino;

$R^4$ is selected from —NR$^6$R$^7$,

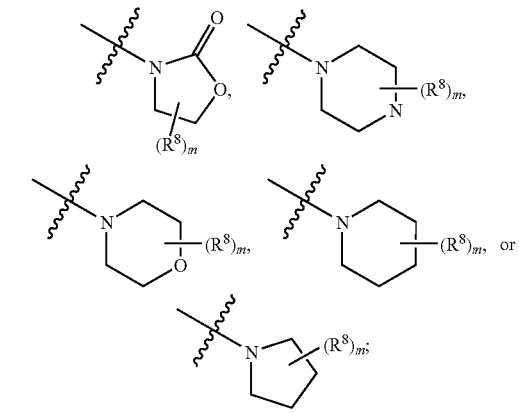

$R^5$ is independently selected from H, OH, NH$_2$, nitro, CN, amide, carboxyl, C$_1$-C$_7$ alkoxy, C$_1$-C$_7$ alkyl, C$_1$-C$_7$ haloalkyl, C$_1$-C$_7$ haloalkyloxy, C$_1$-C$_7$ hydroxyalkyl, C$_1$C$_7$ alkenyl, C$_1$-C$_7$ alkyl-C(=O)O—, C$_1$-C$_7$alkyl-C(=O)—, C$_1$-C$_7$ alkynyl, halo, hydroxyalkoxy, C$_1$-C$_7$ alkyl-NHSO$_2$—, C$_1$-C$_7$ alkyl-SO$_2$NH—, C$_1$-C$_7$ alkylsulfonyl, C$_1$-C$_7$ alkylamino or di(C$_1$-C$_7$)alkylamino;

$R^6$ is independently selected from H, C$_1$-C$_4$ alkyl or C(O)R$^9$;

$R^7$ is selected from H, —(CR$^a_2$)$_v$O(CR$^a_2$)$_q$R$^{12}$, —(CR$^a_2$)$_s$C(O)(CR$^a_2$)$_q$R$^{13}$, —(CR$^a_2$)$_s$C(O)O(CR$^a_2$)$_q$R$^{12}$, —(CR$^a_2$)$_s$C(O)NHR$^{11}$, —(CR$^a_2$)$_q$R$^{10}$, —(CR$^a_2$)$_s$SO$_2$NHR$^{11}$, —(CR$^a_2$)$_v$NHR$^{11}$;

$R^8$ is independently selected from H, C$_1$-C$_4$ alkyl, N(R$^6$)$_2$, —(CR$^a_2$)$_q$R$^{12}$ or when m is at least 2, two adjacent R$^8$ form an aryl ring;

$R^9$ is selected from H or C$_1$-C$_4$ alkyl;

$R^{10}$ is selected from H, substituted or unsubstituted C$_1$-C$_7$ alkyl, substituted or unsubstituted C$_3$-C$_8$ cycloalkyl, substituted or unsubstituted heterocyclic, substituted or unsubstituted heteroaryl or substituted or unsubstituted aryl;

$R^{11}$ is independently selected from H, substituted or unsubstituted C$_1$-C$_7$ alkyl, substituted or unsubstituted C$_3$-C$_8$ cycloalkyl, substituted or unsubstituted heterocyclic, substituted or unsubstituted heteroaryl, substituted or unsubstituted aryl, substituted or unsubstituted $C_3$-$C_8$ alkylcycloalkyl, substituted or unsubstituted alkylheterocyclic, substituted or unsubstituted alkylheteroaryl or substituted or unsubstituted alkylaryl;

$R^{12}$ is independently selected from H, substituted or unsubstituted $C_1$-$C_7$ alkyl, substituted or unsubstituted $C_3$-$C_8$ cycloalkyl, substituted or unsubstituted heteroaryl, substituted or unsubstituted heterocyclic or substituted or unsubstituted aryl;

$R^{13}$ is selected from H, substituted or unsubstituted $C_1$-$C_7$ alkyl, substituted or unsubstituted $C_3$-$C_8$ cycloalkyl, substituted or unsubstituted heteroaryl, substituted or unsubstituted heterocyclic or substituted or unsubstituted aryl;

Ring B is aryl or heteroaryl;

Ring Het is pyridyl or pyrimidinyl;

$R^a$ is independently selected from H or $C_1$-$C_4$ alkyl;

m is 1, 2, 3, 4, 5, 6, 7, 8, 9 or 10;

n is 1 or 2;

p is 1, 2, 3 or 4;

s and q are independently 0, 1, 2, 3, or 4;

t and v are independently 1, 2, 3 or 4;

$L^1$ is $(CH_2)_r$, ethenyl or cyclopropyl, wherein r is 0, 1 or 2;

$L^2$ is a bond or $(CR^1R^2)_n$;

X is OH, SH or $NH_2$;

or a stereoisomer or pharmaceutically acceptable salt thereof.

In another embodiment of the invention, the compounds of the invention are represented by Formula IA:

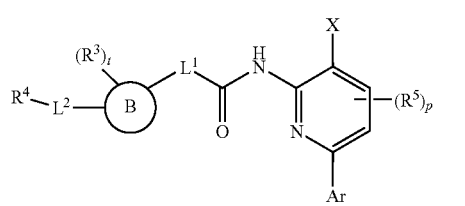

IA

In another embodiment of the invention, the compounds of the invention are represented by Formula II:

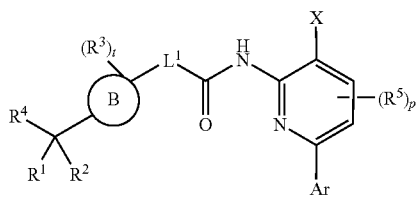

II wherein Ar is phenyl, thienyl or pyridyl, optionally substituted with halo, methyl, methoxy, amino, hydroxyl or halomethyl;

$R^1$ and $R^2$ are independently selected from H, OH, halo, $NH_2$, $C_1$-$C_4$ alkyl, or $C_1$-$C_4$ alkoxy;

$R^3$ is independently selected from H, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino;

$R^4$ is selected from —$NR^6R^7$;

$R^5$ is independently selected from H, OH, $NH_2$, nitro, CN, amide, carboxyl, $C_1$-$C_2$ alkoxy, $C_1$-$C_2$ alkyl, $C_1$-$C_2$ haloalkyl, $C_1$-$C_2$ haloalkyloxy, $C_1$-$C_2$ hydroxyalkyl, $C_1$-$C_2$ alkenyl, $C_1$-$C_2$ alkyl-C(=O)O—, $C_1$-$C_2$ alkyl-C(=O)—, $C_1$-$C_2$ alkynyl, halo, hydroxyalkoxy, $C_1$-$C_2$ alkyl-$NHSO_2$—, $C_1$-$C_2$ alkyl-$SO_2NH$—, $C_1$-$C_2$ alkylsulfonyl, $C_1$-$C_2$ alkylamino or di($C_1$-$C_2$)alkylamino;

$R^6$ is independently selected from H or $C_1$-$C_4$ alkyl;

$R^7$ is selected from —$(CR^a_2)_sC(O)(CR^a_2)_qR^{13}$, or —$(CR^a_2)_sC(O)O(CR^a_2)_qR^{12}$;

$R^{12}$ is selected from H, $C_1$-$C_4$ alkyl, $C_3$-$C_6$ cycloalkyl, heteroaryl, aryl or heterocyclic, wherein the alkyl, cycloalkyl, heteroaryl, heterocyclic or aryl is optionally substituted with aryl, heteroaryl, halo, $C_1$-$C_4$ alkyl, $N(R^6)_2$, OH, $C_1$-$C_4$ alkoxy or $C_1$-$C_4$ haloalkyl;

$R^{13}$ is selected from H, $C_2$-$C_7$ alkyl, $C_3$-$C_6$ cycloalkyl, heteroaryl, or aryl, wherein the cycloalkyl, heteroaryl or aryl is optionally substituted with aryl, heteroaryl, halo, $C_1$-$C_4$ alkyl, $N(R^6)_2$, OH, $C_1$-$C_4$ alkoxy or $C_1$-$C_4$ haloalkyl;

$R^a$ is independently selected from H or $C_1$-$C_4$ alkyl;

Ring B is aryl or heteroaryl;

p is 1, 2, 3 or 4;

s and q are independently 0, 1, 2, 3, or 4;

$L^1$ is $(CH_2)_r$, ethenyl or cyclopropyl, wherein r is 0, 1 or 2;

X is OH or $NH_2$;

or a stereoisomer or pharmaceutically acceptable salt thereof

In another embodiment of the invention,

Ar is

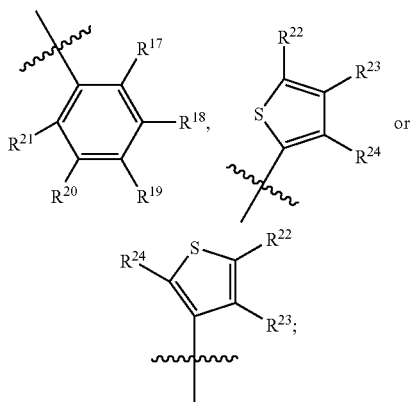

$R^1$ and $R^2$ are H;

$R^3$ is H;

$R^4$ is —$NR^6R^7$;

$R^5$ is H;

$R^6$ is selected from H or $C_1$-$C_4$ alkyl;

$R^7$ is —$C(O)(CR^a_2)_qR^{13}$;

$R^{13}$ is selected from H, $C_2$-$C_7$ alkyl, cycloalkyl, aryl or heteroaryl;

$R^{17}$ and $R^{21}$ are independently selected from hydrogen or fluoro;

$R^{18}$, $R^{19}$ or $R^{20}$ are independently selected from hydrogen, halo, methyl, methoxy or halomethyl;

$R^{22}$, $R^{23}$ and $R^{24}$ are independently selected from hydrogen, methyl, amino, hydroxyl, and halo;

Ring B is aryl or heteroaryl;

$R^a$ is independently H or $C_1$-$C_4$ alkyl;

q is independently 0, 1 or 2;
L¹ is a bond;
X is NH₂;
In a further embodiment of the invention, Ar is phenyl or thienyl.
In another embodiment of the invention, Ring B is

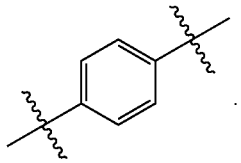 [SMILES: *c1ccc(*)cc1]

In one embodiment of the invention,

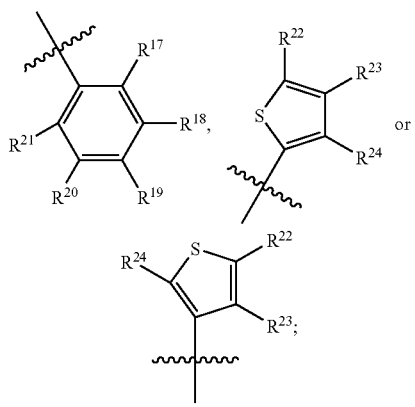

$R^1$ and $R^2$ are H;
$R^3$ is H;
$R^4$ is —$NR^6R^7$;
$R^5$ is H;
$R^6$ is selected from H or $C_1$-$C_4$ alkyl;
$R^7$ is —$C(O)O(CR^a{}_2)_qR^{12}$;
$R^{12}$ is selected from H, $C_1$-$C_4$ alkyl, cycloalkyl, aryl, or heteroaryl;
$R^{17}$ and $R^{21}$ are independently selected from hydrogen or fluoro;
$R^{18}$, $R^{19}$ or $R^{20}$ are independently selected from hydrogen, halo, methyl, methoxy or halomethyl;
$R^{22}$, $R^{23}$ and $R^{24}$ are independently selected from hydrogen, methyl, amino, hydroxyl or halo;
$R^a$ is independently H or $C_1$-$C_4$ alkyl;
Ring B is aryl or heteroaryl;
q is independently 0, 1 or 2;
L¹ is a bond;
X is NH₂.
In another embodiment of the invention, Ar is phenyl. In a further embodiment, Ring B is

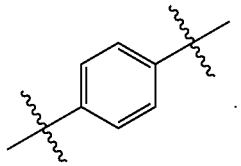 [SMILES: *c1ccc(*)cc1]

In one embodiment of the invention, the following formula is provided:

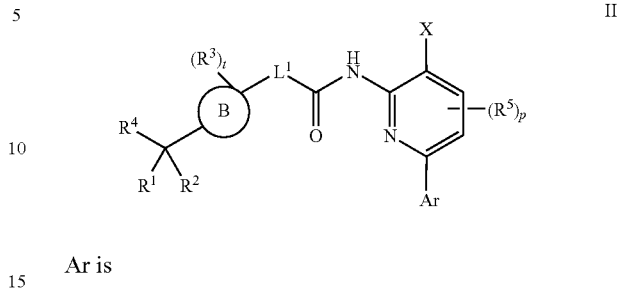

Ar is

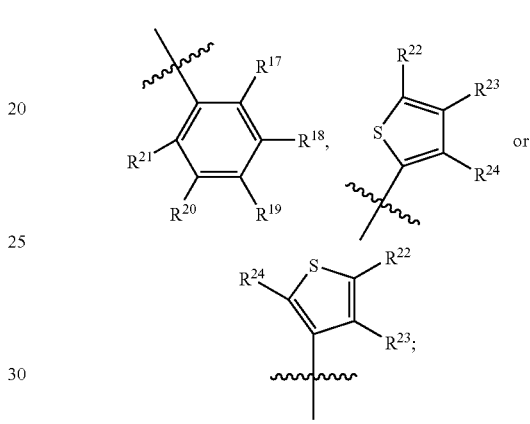

$R^1$ and $R^2$ are independently selected from H, OH, halo, NH₂, $C_1$-$C_4$ alkyl, or $C_1$-$C_4$ alkoxy;
$R^3$ is H;
$R^4$ is —$NR^6R^7$;
$R^5$ is H;
$R^6$ is selected from H or $C_1$-$C_4$ alkyl;
$R^7$ is —$C(O)O(CR^a{}_2)_qR^{12}$;
$R^{12}$ is selected from aryl, heterocyclic or heteroaryl; wherein the aryl, heterocyclic or heteroaryl is optionally substituted with OH, NH₂, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO₂—, $C_1$-$C_7$ alkyl-SO₂NH—, $C_1$-$C_7$ alkylsulfonyl, $C_1$-$C_7$ alkylamino or di($C_1$-$C_7$)alkylamino, aryl, heterocyclic or cycloalkyl;
$R^{17}$ and $R^{21}$ are independently selected from hydrogen or fluoro;
$R^{18}$, $R^{19}$ or $R^{20}$ are independently selected from hydrogen, halo, methyl, methoxy or halomethyl;
$R^{22}$, $R^{23}$ and $R^{24}$ are independently selected from hydrogen, methyl, amino, hydroxyl or halo;
$R^a$ is independently H or $C_1$-$C_4$ alkyl;
Ring B is aryl or heteroaryl;
q is independently 0, 1 or 2;
L¹ is a bond;
X is NH₂.
In one embodiment, $R^{12}$ is selected from aryl or heteroaryl.
In one embodiment, $R^{12}$ is selected from aryl or heteroaryl, optionally substituted with OH, NH₂, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino, aryl, heterocyclic or cycloalkyl;

In one embodiment, $R^{12}$ is phenyl, wherein the phenyl is optionally substituted with OH, NH$_2$, nitro, CN, amide, carboxyl, $C_1$-$C_4$ alkoxy, $C_1$-$C_4$ alkyl, $C_1$-$C_4$ haloalkyl, $C_1$-$C_4$ haloalkyloxy, $C_1$-$C_4$ hydroxyalkyl, $C_1$-$C_4$ alkenyl, $C_1$-$C_4$ alkyl-C(=O)O—, $C_1$-$C_4$ alkyl-C(=O)—, $C_1$-$C_4$ alkynyl, halo, hydroxyalkoxy, $C_1$-$C_4$ alkyl-NHSO$_2$—, $C_1$-$C_4$ alkyl-SO$_2$NH—, $C_1$-$C_4$ alkylsulfonyl, $C_1$-$C_4$ alkylamino or di($C_1$-$C_4$)alkylamino.

In another embodiment, $R^{12}$ is phenyl, wherein the phenyl is optionally substituted with OH, NH$_2$, nitro, CN, amide, carboxyl, $C_1$-$C_2$ alkoxy, $C_1$-$C_2$ alkyl, $C_1$-$C_2$ haloalkyl, $C_1$-$C_2$ haloalkyloxy, $C_1$-$C_2$ hydroxyalkyl, $C_1$-$C_2$ alkenyl, $C_1$-$C_2$ alkyl-C(=O)O—, $C_1$-$C_2$ alkyl-C(=O)—, $C_1$-$C_2$ alkynyl, halo, hydroxyalkoxy, $C_1$-$C_2$ alkyl-NHSO$_2$—, $C_1$-$C_2$ alkyl-SO$_2$NH—, $C_1$-$C_2$ alkylsulfonyl, $C_1$-$C_2$ alkylamino or di($C_1$-$C_2$)alkylamino.

In one embodiment, $R^{12}$ is 2-pyridyl, wherein the 2-pyridyl is optionally substituted with OH, NH$_2$, nitro, CN, amide, carboxyl, $C_1$-$C_4$ alkoxy, $C_1$-$C_4$ alkyl, $C_1$-$C_4$ haloalkyl, $C_1$-$C_4$ haloalkyloxy, $C_1$-$C_4$ hydroxyalkyl, $C_1$-$C_4$ alkenyl, $C_1$-$C_4$ alkyl-C(=O)O—, $C_1$-$C_4$ alkyl-C(=O)—, $C_1$-$C_4$ alkynyl, halo, hydroxyalkoxy, $C_1$-$C_4$ alkyl-NHSO$_2$—, $C_1$-$C_4$ alkyl-SO$_2$NH—, $C_1$-$C_4$ alkylsulfonyl, $C_1$-$C_4$ alkylamino or di($C_1$-$C_4$)alkylamino.

In another embodiment, $R^{12}$ is 2-pyridyl, wherein the 2-pyridyl is optionally substituted with OH, NH$_2$, nitro, CN, amide, carboxyl, $C_1$-$C_2$ alkoxy, $C_1$-$C_2$ alkyl, $C_1$-$C_2$ haloalkyl, $C_1$-$C_2$ haloalkyloxy, $C_1$-$C_2$ hydroxyalkyl, $C_1$-$C_2$ alkenyl, $C_1$-$C_2$ alkyl-C(=O)O—, $C_1$-$C_2$ alkyl-C(=O)—, $C_1$-$C_2$ alkynyl, halo, hydroxyalkoxy, $C_1$-$C_2$ alkyl-NHSO$_2$—, $C_1$-$C_2$ alkyl-SO$_2$NH—, $C_1$-$C_2$ alkylsulfonyl, $C_1$-$C_2$ alkylamino or di($C_1$-$C_2$)alkylamino.

In one embodiment, q is 1 or 2.

In one embodiment, $R^a$ is H or $C_1$-$C_2$ alkyl. In another embodiment, $R^a$ is H.

In one embodiment, $R^{12}$ is phenyl and q is 1 or 2. In one embodiment, $R^{12}$ is phenyl and q is 1.

In another embodiment, $R^{12}$ is 2-pyridyl and q is 1 or 2. In another embodiment, $R^{12}$ is 2-pyridyl and q is 1.

In one embodiment, $R^1$ and $R^2$ are H; $R^a$ is H; $R^6$ is H, and q is 1.

In another embodiment, Ar is

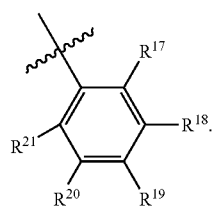

In a further embodiment, Ar is phenyl.
In one embodiment, $R^1$ and $R^2$ are H.

In a further embodiment, Ring B is

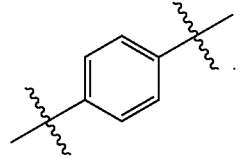 [SMILES: *c1ccc(*)cc1]

Specific embodiments depicting non-limiting Examples of the pyridyl derivatives of the above Formulas are provided in the Experimental Section hereinbelow.

Specific examples of the compounds of the instant invention include:
pyridin-3-ylmethyl{[4-({[3-amino-6-(2-thienyl)pyridin-2yl]amino}carbonyl)phenyl]methyl}carbamate;
methyl[(4-{[(3-amino-6-phenylpyridin-2-yl)amino]carbonyl}phenyl)methyl]carbamate;
Pyridin-3-ylmethyl[(4-{[(3-amino-6-phenylpyridin-2-yl)amino]carbonyl}phenyl)methyl]carbamate;
4-(Acetylamino)-N-(3-amino-6-phenylpyridin-2-yl)benzamide;
ethyl(4-{[(3-amino-6-phenylpyridin-2-yl)amino]carbonyl}benzyl)carbamate;
1-methylethyl(4-{[(3-amino-6-phenylpyridin-2-yl)amino]carbonyl}benzyl)carbamate;
propyl(4-{[(3-amino-6-phenylpyridin-2-yl)amino]carbonyl}benzyl)carbamate;
2-methylpropyl(4-{[(3-amino-6-phenylpyridin-2-yl)amino]carbonyl}benzyl)carbamate;
phenyl(4-{[(3-amino-6-phenylpyridin-2-yl)amino]carbonyl}benzyl)carbamate;
phenylmethyl(4-{[(3-amino-6-phenylpyridin-2-yl)amino]carbonyl}benzyl)carbamate;
4-[(acetylamino)methyl]-N-(3-amino-6-phenylpyridin-2-yl)benzamide;
N-(3-amino-6-phenylpyridin-2-yl)-4-[(propanoylamino)methyl]benzamide;
N-(3-amino-6-phenylpyridin-2-yl)-4-[(butanoylamino)methyl]benzamide;
N-(3-amino-6-phenylpyridin-2-yl)-4-{[(cyclopropylcarbonyl)amino]methyl}benzamide;
N-(3-amino-6-phenylpyridin-2-yl)-4-{[(2-methylpropanoyl)amino]methyl}benzamide;
N-(3-amino-6-phenylpyridin-2-yl)-4-{[(2,2-dimethylpropanoyl)amino]methyl}benzamide;
N-(3-amino-6-phenylpyridin-2-yl)-4-{[(3-methylbutanoylamino]methyl}benzamide;
N-(3-amino-6-phenylpyridin-2-yl)-4-{[(cyclobutylcarbonyl)amino]methyl}benzamide;
N-(3-amino-6-phenylpyridin-2-yl)-4-{[(3-phenylpropanoyl)amino]methyl}benzamide;
N-(3-amino-6-phenylpyridin-2-yl)-4-{[(cyclohexylcarbonyl)amino]methyl}benzamide;
N-(3-amino-6-phenylpyridin-2-yl)-4-{[(cyclopentylcarbonyl)amino]methyl}benzamide;
N-(3-amino-6-phenylpyridin-2-yl)-4-{[(phenylacetyl)amino]methyl}benzamide;
N-(3-amino-6-phenylpyridin-2-yl)-4-{[(phenylcarbonyl)amino]methyl}benzamide;
N-(3-amino-6-phenylpyridin-2-yl)-4-{[(pyridin-2-ylacetyl)amino]methyl}benzamide;
N-(3-amino-6-phenylpyridin-2-yl)-4-{[(pyridin-3-ylacetyl)amino]methyl}benzamide;
N-(3-amino-6-phenylpyridin-2-yl)-4-{[(pyridin-4-ylacetyl)amino]methyl}benzamide;

N-(3-amino-6-phenylpyridin-2-yl)-4-{[(3-pyridin-3-ylpropanoyl)amino]methyl}benzamide;

pyridin-2-ylmethyl(4-{[(3-amino-6-phenylpyridin-2-yl)amino]carbonyl}benzyl)carbamate;

N-(3-amino-6-phenylpyridin-2-yl)-4-({[(methylamino)carbonyl]amino}methyl)benzamide;

N-(3-amino-6-phenylpyridin-2-yl)-4-({[(ethylamino)carbonyl]amino}methyl)benzamide;

N-(3-amino-6-phenylpyridin-2-yl)-4-[(isobutylamino)methyl]benzamide;

N-(3-amino-6-phenylpyridin-2-yl)-4-{[(2-methoxy-1-methylethyl)amino]methyl}benzamide;

N-(3-amino-6-phenylpyridin-2-yl)benzamide;

N-(3-amino-6-phenyl-2-pyridinyl)-4-(1,1-dimethylethyl)benzamide;

benzoic acid, methyl 4-[[(3-amino-6-phenyl-2-pyridinyl)amino]carbonyl]benzoate;

4-(aminomethyl)-N-(3-amino-6-phenyl-2-pyridinyl)benzamide;

2-methoxyethyl(4-{[(3-amino-6-phenylpyridin-2-yl)amino]carbonyl}benzyl)carbamate, tert-Butyl(4-{[(3-amino-6-phenylpyridin-2-yl)amino]carbonyl}benzyl)carbamate;

tert-Butyl(4-{[(2-amino-5-phenylpyridin-3-yl)amino]carbonyl}benzyl)carbamate;

or the pharmaceutically acceptable salt or stereoisomer thereof.

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the heterocyclyl portion of the moiety. In an embodiment, if the number of carbon atoms is not specified, the "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

The term "cycloalkyl" means a monocyclic saturated or unsaturated aliphatic hydrocarbon group having the specified number of carbon atoms. The cycloalkyl is optionally bridged (i.e., forming a bicyclic moiety), for example with a methylene, ethylene or propylene bridge. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, cyclopentenyl, cyclobutenyl and so on.

In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$$CH_2CH(CH_3)$Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbons atoms, and includes a carbocyclic aromatic group fused with a 5-or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to as β-pyridyl) and 4-pyridyl (also referred to as γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thianaphthenyl, pyrazinyland the like.

The term "heterocycle" or "heterocyclyl" as used herein is intended to mean monocyclic, spirocyclic, bicyclic or tricyclic ring of up to 7 atoms in each ring, wherein each ring is aromatic or non-aromatic and contains carbon and from 1 to 4 heteroatoms selected from the group consisting of O, N, P and S. A nonaromatic heterocycle may be fused with an aromatic aryl group such as phenyl or aromatic heterocycle.

"Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, "heterocycle" (also referred to herein as "heterocyclyl"), is a monocyclic, spirocyclic, bicyclic or tricyclic saturated or unsaturated ring of 5- to 14-ring atoms of carbon and from one to four heteroatoms selected from O, N, S or P. Examples of heterocyclic rings include, but are not limited to: pyrrolidinyl, piperidinyl, morpholinyl, thiamorpholinyl, piperazinyl, dihydrofuranyl, tetrahydrofuranyl, dihydropyranyl, tetrahydrodropyranyl, dihydroquinolinyl, tetrahydroquinolinyl, dihydroisoquinolinyl, tetrahydroisoquinolinyl, dihydropyrazinyl, tetrahydropyrazinyl, dihydropyridyl, tetrahydropyridyl and the like.

An "alkylaryl group" (arylalkyl) is an alkyl group substituted with an aromatic group, for example, a phenyl group. A preferred alkylaryl group is a benzyl group. Suitable aromatic groups are described herein and suitable alkyl groups are described herein.

An "alkylheteroaryl group" (heteroarylalkyl) is an alkyl group substituted with a heteroaryl group. Suitable heteroaryl groups are described herein and suitable alkyl groups are described herein.

An "alkylheterocyclyl" group" is an alkyl group substituted with a heterocyclyl group. Suitable heterocyclyl groups are described herein and suitable alkyl groups are described herein. Suitable substituents for an alkyheterocyclyl group are described herein.

An "alkylcycloalkyl group" is an alkyl group substituted with a cycloalkyl group. Suitable cycloalkyl groups are described herein and suitable alkyl groups are described herein.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

When a moiety is referred to as "unsubstituted" or not referred to as "substituted" or "optionally substituted", it means that the moiety does not have any substituents. When a moiety is referred to as substituted, it denotes that any portion of the moiety that is known to one skilled in the art as being available for substitution can be substituted. The phrase "optionally substituted with one or more substituents" means, in one embodiment, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

In one embodiment, Ar is phenyl, thienyl or pyridyl, optionally substituted with halo, methyl, methoxy amino, hydroxyl or halomethyl. In one embodiment, Ar is

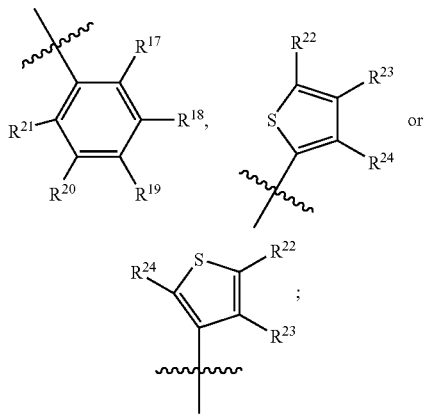

$R^{17}$ and $R^{21}$ are independently selected from hydrogen or fluoro;

$R^{18}$, $R^{19}$ or $R^{20}$ are independently selected from hydrogen, halo, methyl, methoxy or halomethyl;

$R^{22}$, $R^{23}$ and $R^{24}$ are independently selected from hydrogen, methyl, amino, hydroxyl, and halo.

In one embodiment, Ar is

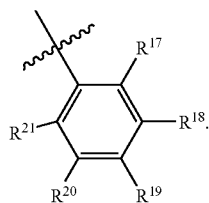

In one embodiment, $R^{17}$ and $R^{21}$ are independently selected from hydrogen or fluoro; $R^{18}$, $R^{19}$ or $R^{20}$ independently independently selected from hydrogen, halo, methyl, methoxy or halomethyl.

In another embodiment, $R^{17}$, $R^{18}$, $R^{20}$, and $R^{21}$ are independently selected from hydrogen or fluoro; $R^{19}$ is independently selected from hydrogen, halo, methyl, methoxy or halomethyl.

In one embodiment, Ar is

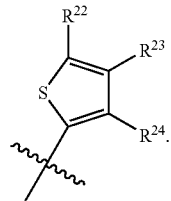

In another embodiment, Ar is

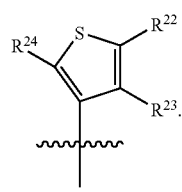

In one embodiment, $R^{22}$, $R^{23}$ and $R^{24}$ are independently selected from hydrogen, methyl, and halo.

In another embodiment, Ar is phenyl or thienyl. In a further embodiment, Ar is phenyl.

In one embodiment, $R^1$ and $R^2$ are independently selected from H, OH, halo, NH$_2$, C$_1$-C$_4$ alkyl, or C$_1$-C$_{10}$ alkoxy. In one embodiment, $R^1$ and $R^2$ are independently selected from H, OH, halo, NH$_2$, C$_1$-C$_2$ alkyl, or C$_1$-C$_2$ alkoxy. In another embodiment, $R^1$ and $R^2$ are H. In one embodiment, $R^1$ and $R^2$ are independently selected from H, OH, halo, NH$_2$, C$_1$-C$_4$ alkyl, C$_1$-C$_4$ alkenyl, C$_1$-C$_4$ alkynyl, C$_1$-C$_4$ alkoxy, C$_3$-C$_6$ cycloalkyl, heteroaryl, heterocyclic or aryl, wherein the cycloalkyl, heteroaryl, heterocyclic or aryl is optionally substituted with OH, NH$_2$, nitro, CN, amide, carboxyl, C$_1$-C$_7$ alkoxy, C$_1$-C$_7$ alkyl, C$_1$-C$_7$ haloalkyl, C$_1$-C$_7$ haloalkyloxy, C$_1$-C$_7$ hydroxyalkyl, C$_1$-C$_7$ alkenyl, C$_1$-C$_7$alkyl-C(=O)O—, C$_1$-C$_7$ alkyl-C(=O)—, C$_1$-C$_7$ alkynyl, halo, hydroxyalkoxy, C$_1$-C$_7$ alkyl-NHSO$_2$—, C$_1$-C$_7$ alkyl-SO$_2$NH—, C$_1$-C$_7$ alkylsulfonyl, C$_1$-C$_7$ alkylamino or di(C$_1$-C$_7$)alkylamino.

In one embodiment, $R^3$ is H.

In one embodiment, $R^4$ is selected from —NR$^6$R$^7$,

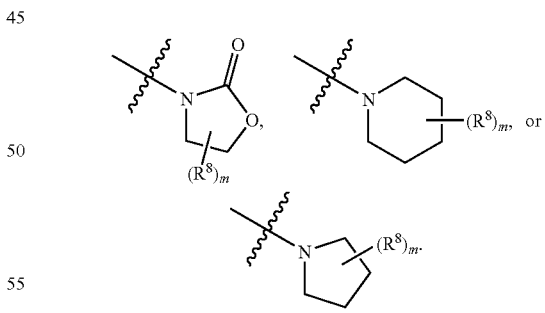

In another embodiment, $R^4$ is —NR$^6$R$^7$.

In one embodiment, $R^5$ is H. In another embodiment, $R^5$ is independently selected from H, OH, NH$_2$, nitro, CN, amide, carboxyl, C$_1$-C$_2$ alkoxy, C$_1$-C$_2$ alkyl, C$_1$-C$_2$ haloalkyl, C$_1$-C$_2$ haloalkyloxy, C$_1$-C$_2$ hydroxyalkyl, C$_1$-C$_2$ alkenyl, C$_1$-C$_2$alkyl-C(=O)O—, C$_1$-C$_2$ alkyl-C(=O)—, C$_1$-C$_2$ alkynyl, halo, hydroxyalkoxy, C$_1$-C$_2$ alkyl-NHSO$_2$—, C$_1$-C$_2$ alkyl-SO$_2$NH—, C$_1$-C$_2$ alkylsulfonyl, C$_1$-C$_2$ alkylamino or di(C$_1$-C$_2$)alkylamino. In a further embodiment, $R^5$ is independently selected from H, OH, NH$_2$, nitro, CN, amide, carboxyl, $C_1$-$C_4$ alkoxy, $C_1$-$C_4$ alkyl, $C_1$-$C_4$ haloalkyl, $C_1$-$C_4$ haloalkyloxy, $C_1$-$C_4$ hydroxyalkyl, $C_1$-$C_4$ alkenyl, $C_1$-$C_4$ alkyl-C(=O)O—, $C_1$-$C_4$ alkyl-C(=O)—, $C_1$-$C_4$ alkynyl, halo, hydroxyalkoxy, $C_1$-$C_4$ alkyl-NHSO$_2$—, $C_1$-$C_4$ alkyl-SO$_2$NH—, $C_1$-$C_4$ alkylsulfonyl, $C_1$-$C_4$ alkylamino or di($C_1$-$C_4$)alkylamino.

In one embodiment, $R^6$ is selected from H or $C_1$-$C_4$ alkyl. In one embodiment, $R^6$ is selected from H or $C_1$-$C_2$ alkyl. In one embodiment, $R^6$ is H.

In one embodiment, $R^7$ is selected from H, —(CR$^a_2$)$_v$O(CR$^a_2$)$_q$R$^{12}$, —C(O)(CR$^a_2$)$_q$R$^{13}$, —(CR$^a_2$)$_v$C(O)NHR$^{11}$ or —(CR$^a_2$)$_v$NHR$^{11}$. In one embodiment, $R^7$ is selected from H, —(CR$^a_2$)$_v$O(CR$^a_2$)$_q$R$^{12}$, —C(O)(CR$^a_2$)$_q$R$^{13}$ or —(CR$^a_2$)$_v$NHR$^{11}$. In another embodiment, $R^7$ is selected from —C(O)(CR$^a_2$)$_q$R$^{13}$ or —(CR$^a_2$)$_v$NHR$^{11}$. In another embodiment, $R^7$ is —C(O)(CR$^a_2$)$_q$R$^{13}$. In one embodiment, $R^7$ is —C(O)O(CR$^a_2$)$_q$R$^{12}$. In one embodiment, $R^7$ is —C(O)OCH$_2$R$^{12}$.

In one embodiment, $R^8$ is independently selected from H, $C_1$-$C_4$ alkyl, N(R$^6$)$_2$, —(CR$^a_2$)$_q$R$^{12}$ or when m is at least 2, two adjacent $R^8$ form an aryl ring.

In one embodiment, $R^9$ is H or $C_1$-$C_4$ alkyl.

In one embodiment, $R^{10}$ is selected from H, $C_1$-$C_4$ alkyl, $C_3$-$C_6$ cycloalkyl, heteroaryl, aryl or heterocyclic, wherein the alkyl, cycloalkyl, heteroaryl, heterocyclic, or aryl is optionally substituted with aryl, heteroaryl, halo, $C_1$-$C_4$ alkyl, N(R$^6$)$_2$, OH, $C_1$-$C_4$ alkoxy or $C_1$-$C_4$ haloalkyl. In one embodiment, $R^{10}$ is selected from H, $C_1$-$C_4$ alkyl, $C_3$-$C_6$ cycloalkyl, heteroaryl, aryl or heterocyclic, wherein the alkyl, cycloalkyl, heteroaryl, heterocyclic, or aryl is optionally substituted with OH, NH$_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$alkyl-C(=O)O—, $C_1$-$C_7$ alkyl-C(=O)—, $C_1$-$C_7$ alkynyl, halo, hydroxyalkoxy, $C_1$-$C_7$alkyl-NHSO$_2$—, $C_1$-$C_7$alkyl-SO$_2$NH—, $C_1$-$C_7$ alkylsulfonyl, $C_1$-$C_7$ alkylamino or di($C_1$-$C_7$)alkylamino, aryl, heterocyclic, or cycloalkyl.

In another embodiment, $R^{10}$ is selected from H, $C_1$-$C_4$ alkyl, cycloalkyl, aryl, or heteroaryl. In another embodiment, $R^{10}$ is selected from $C_1$-$C_4$ alkyl or heteroaryl. In a further embodiment, $R^{10}$ is heteroaryl. In a particular embodiment, $R^{10}$ is pyridyl. In a particular embodiment, $R^{10}$ is pyridin-3-yl. In a particular embodiment, $R^{10}$ is pyridin-4-yl. In a particular embodiment, $R^{10}$ is pyridin-2-yl. In one embodiment, $R^{10}$ is methyl. In another embodiment, $R^{10}$ is ethyl. In a further embodiment, $R^{10}$ is propyl.

In one embodiment, $R^{11}$ is independently selected from H, $C_1$-$C_4$ alkyl, $C_3$-$C_6$ cycloalkyl, heteroaryl, aryl, heterocyclic, $C_3$-$C_6$ alkylcycloalkyl, alkylheteroaryl, alkylaryl or alkylheterocyclic, wherein the alkyl, cycloalkyl, heteroaryl, heterocyclic, aryl, alkylcycloalkyl, alkylheteroaryl, alkylheterocyclic, or alkylaryl is optionally substituted with aryl, heteroaryl, halo, $C_1$-$C_4$ alkyl, N(R$^6$)$_2$, OH, $C_1$-$C_4$ alkoxy or $C_1$-$C_4$ haloalkyl.

In one embodiment, $R^{11}$ is independently selected from H, $C_1$-$C_4$ alkyl, $C_3$-$C_6$ cycloalkyl, heteroaryl, aryl, heterocyclic, $C_3$-$C_6$ alkylcycloalkyl, alkylheteroaryl, alkylaryl or alkylheterocyclic, wherein the alkyl, cycloalkyl, heteroaryl, heterocyclic, aryl, alkylcycloalkyl, alkylheteroaryl, alkylheterocyclic, or alkylaryl is optionally substituted with OH, NH$_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino, aryl, heterocyclic or cycloalkyl.

In another embodiment, $R^{11}$ is selected from H, $C_1$-$C_4$ alkyl, cycloalkyl, alkylcycloalkyl, aryl, alkylaryl, alkylheteroaryl or heteroaryl. In another embodiment, $R^{11}$ is selected from $C_1$-$C_4$ alkyl or alkylheteroaryl. In a further embodiment, $R^{11}$ is alkylheteroaryl. In a particular embodiment, $R^{11}$ is —CH$_2$-pyridyl. In a particular embodiment, $R^{11}$ is —CH$_2$-pyridin-3-yl. In a particular embodiment, $R^{11}$ is —CH$_2$-pyridin-4-yl. In a particular embodiment, $R^{11}$ is —CH$_2$-pyridin-2-yl. In one embodiment, $R^{11}$ is methyl. In another embodiment, $R^{11}$ is ethyl. In a further embodiment, $R^{11}$ is propyl.

In one embodiment, $R^{12}$ is selected from H, $C_1$-$C_4$ alkyl, $C_3$-$C_6$ cycloalkyl, heteroaryl, aryl or heterocyclic, wherein the alkyl, cycloalkyl, heteroaryl, heterocyclic or aryl is optionally substituted with aryl, heteroaryl, halo, $C_1$-$C_4$ alkyl, N(R$^6$)$_2$, OH, $C_1$-$C_4$ alkoxy or $C_1$-$C_4$ haloalkyl. In one embodiment, $R^{12}$ is selected from H, $C_1$-$C_4$ alkyl, $C_3$-$C_6$ cycloalkyl, heteroaryl, aryl or heterocyclic, wherein the alkyl, cycloalkyl, heteroaryl, heterocyclic or aryl is optionally substituted with OH, NH$_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino, aryl, heterocyclic or cycloalkyl.

In one embodiment, $R^{12}$ is selected from heterocyclic, heteroaryl or aryl. In another embodiment, $R^{12}$ is selected from heteroaryl or aryl. In a further embodiment, $R^{12}$ is selected from phenyl or 2-pyridyl. In a further embodiment, $R^{12}$ is furanyl, thiophenyl or pyranyl. In one embodiment, $R^{12}$ is phenyl.

In one embodiment, $R^{12}$ is optionally substituted with aryl, heteroaryl, halo, $C_1$-$C_4$ alkyl, N(R$^6$)$_2$, OH, $C_1$-$C_4$ alkoxy or $C_1$-$C_4$ haloalkyl. In one embodiment, $R^{12}$ is optionally substituted with OH, NH$_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino, aryl, heterocyclic or cycloalkyl.

In another embodiment, $R^{12}$ is optionally substituted with OH, NH$_2$, nitro, CN, amide, carboxyl, $C_1$-$C_4$ alkoxy, $C_1$-$C_4$ alkyl, $C_1$-$C_4$ haloalkyl, $C_1$-$C_4$ haloalkyloxy, $C_1$-$C_4$ hydroxyalkyl, $C_1$-$C_4$ alkenyl, $C_1$-$C_4$alkyl-C(=O)O—, $C_1$-$C_4$ alkyl-C(=O)—, $C_1$-$C_4$ alkynyl, halo, hydroxyalkoxy, $C_1$-$C_4$ alkyl-NHSO$_2$—, $C_1$-$C_4$ alkyl-SO$_2$NH—, $C_1$-$C_4$ alkylsulfonyl, $C_1$-$C_4$ alkylamino or di($C_1$-$C_4$)alkylamino.

In a further embodiment, $R^{12}$ is optionally substituted with OH, NH$_2$, nitro, CN, amide, carboxyl, $C_1$-$C_2$ alkoxy, $C_1$-$C_2$ alkyl, $C_1$-$C_2$ haloalkyl, $C_1$-$C_2$ haloalkyloxy, $C_1$-$C_2$ hydroxyalkyl, $C_1$-$C_2$ alkenyl, $C_1$-$C_2$ alkyl-C(=O)O—, $C_1$-$C_2$ alkyl-C(=O)—, $C_1$-$C_2$ alkynyl, halo, hydroxyalkoxy, $C_1$-$C_2$alkyl-NHSO$_2$—, $C_1$-$C_2$alkyl-SO$_2$NH—, $C_1$-$C_2$ alkylsulfonyl, $C_1$-$C_2$ alkylamino or di($C_1$-$C_2$)alkylamino.

In a further embodiment, $R^{12}$ is optionally substituted with $C_1$-$C_2$ alkyl. In a further embodiment, $R^{12}$ is optionally substituted with $C_1$-$C_4$ alkyl.

In another embodiment, $R^{12}$ is selected from H, $C_1$-$C_4$ alkyl, cycloalkyl, aryl, or heteroaryl. In another embodiment, $R^{12}$ is selected from $C_1$-$C_4$ alkyl or heteroaryl. In a further embodiment, $R^{12}$ is heteroaryl. In a particular embodiment, $R^{12}$ is pyridyl. In a particular embodiment, $R^{12}$ is pyridin-3-yl. In a particular embodiment, $R^{12}$ is pyridin-4-yl. In a particular embodiment, $R^{12}$ is pyridin-2-yl. In one embodiment, $R^{12}$ is methyl. In another embodiment, $R^{12}$ is ethyl. In a further embodiment, $R^{12}$ is propyl.

In one embodiment, $R^{12}$ is pyridin-2-yl, and optionally substituted with $C_1$-$C_4$ alkyl. In another embodiment, $R^{12}$ is pyridin-2-yl, and optionally substituted with $C_1$-$C_2$ alkyl.

In one embodiment, $R^{12}$ is

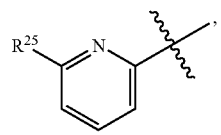

and $R^{25}$ is $C_1$-$C_4$ alkyl. In another embodiment, $R^{25}$ is $C_1$-$C_2$ alkyl.

In one embodiment, $R^{13}$ is selected from H, $C_2$-$C_7$ alkyl, $C_3$-$C_8$ cycloalkyl, heteroaryl, or aryl, wherein the cycloalkyl, heteroaryl or aryl is optionally substituted with aryl, heteroaryl, halo, $C_1$-$C_4$ alkyl, $N(R^6)_2$, OH, $C_1$-$C_4$ alkoxy or $C_1$-$C_4$ haloalkyl. In one embodiment, $R^{13}$ is selected from H, $C_2$-$C_7$ alkyl, $C_3$-$C_8$ cycloalkyl, heteroaryl, or aryl, wherein the cycloalkyl, heteroaryl or aryl is optionally substituted with OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino, aryl, heterocyclic or cycloalkyl.

In another embodiment, $R^{13}$ is selected from H, $C_1$-$C_4$ alkyl, cycloalkyl, aryl, or heteroaryl. In another embodiment, $R^{13}$ is selected from $C_1$-$C_4$ alkyl or heteroaryl. In a further embodiment, $R^{13}$ is heteroaryl. In a particular embodiment, $R^{13}$ is pyridyl. In a particular embodiment, $R^{13}$ is pyridin-3-yl. In a particular embodiment, $R^{13}$ is pyridin-4-yl. In a particular embodiment, $R^{13}$ is pyridin-2-yl. In one embodiment, $R^{13}$ is methyl. In another embodiment, $R^{13}$ is ethyl. In a further embodiment, $R^{13}$ is propyl.

In one embodiment, $R^a$ is H. In another embodiment, $R^a$ is H or $C_1$-$C_2$ alkyl. In another embodiment, $R^a$ is H or $C_1$-$C_4$ alkyl.

In one embodiment, Ring B is selected from phenyl, benzothiophenyl, benzofuranyl, thiazolyl, benzothiazolyl, furanyl, pyridyl, pyrimidyl, quinolinyl, thiophenyl, benzodioxyl, benzooxadiazolyl, quinoxalinyl, benzotriazolyl, benzoimidazolyl or benzooxazolyl. In another embodiment, Ring B is phenyl, benzothiophenyl, thiophenyl or pyridyl. In a further embodiment, Ring B is phenyl or pyridyl. In a further embodiment, Ring B is phenyl.

In one embodiment, Ring Het is pyrimidinyl. In one embodiment, Ring Het is

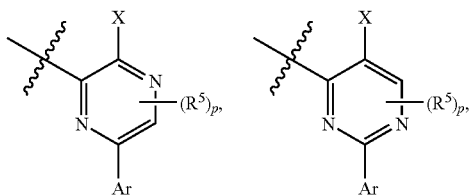

-continued

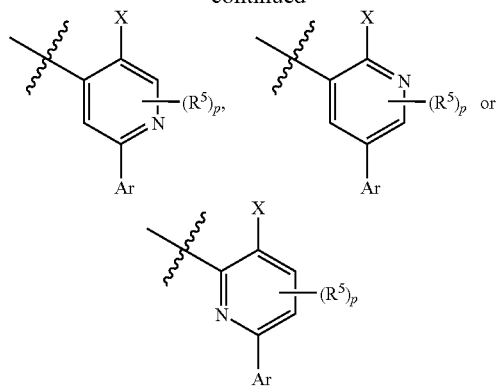

In one embodiment, m is 1, 2, 3, 4, 5, 6, 7, or 8. In another embodiment, m is 1 or 2.

In one embodiment, n is 1 or 2. In another embodiment, n is 1.

In one embodiment, p is 1, 2, 3 or 4. In another embodiment, p is 1.

In one embodiment, q is independently 0, 1, 2, 3, or 4. In another embodiment, q is independently 0, 1 or 2. In a further embodiment, q is 0. In a further embodiment, q is 1. In a further embodiment, q is 2.

In one embodiment, t is 1 or 2. In one embodiment, v is 1 or 2.

In one embodiment, $L^1$ is ethenyl or a bond. In another embodiment, $L^1$ is a bond.

In one embodiment, $L^2$ is $CR^1R^2$. In another embodiment, $L^2$ is a bond.

In one embodiment, X is OH or $NH_2$. In another embodiment, X is $NH_2$.

Stereochemistry

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the pyridyl and pyrimidinyl derivatives disclosed herein. A prodrug of any of the compounds can be made using well-known pharmacological techniques.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

Pharmaceutically Acceptable Salts

The pyridyl and pyrimidinyl derivatives described herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, phosphoric acid, trifluoroacetic acid, formic acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also be formed from elemental anions such as chlorine, bromine and iodine.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The invention also relates to methods of using the pyridyl and pyrimidinyl derivatives described herein. As demonstrated herein, the pyridyl and pyrimidinyl derivatives of the present invention are useful for the treatment of cancer. In addition, there is a wide range of other diseases for which pyridyl and pyrimidinyl derivatives may be found useful. Non-limiting examples are thioredoxin (TRX)-mediated diseases as described herein, and diseases of the central nervous system (CNS) as described herein.

1. Treatment of Cancer

As demonstrated herein, the pyridyl and pyrimidinyl derivatives of the present invention are useful for the treatment of cancer. Accordingly, in one embodiment, the invention relates to a method of treating cancer in a subject in need of treatment comprising administering to said subject a therapeutically effective amount of the pyridyl and pyrimidinyl derivatives described herein.

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma, vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

In an embodiment, the instant compounds are useful in the treatment of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

2. Treatment of Thioredoxin (TRX)-Mediated Diseases

In another embodiment, the pyridyl and pyrimidinyl derivatives are used in a method of treating a thioredoxin (TRX)-mediated disease or disorder in a subject in need thereof, comprising administering to the subject a therapeutically effective amount of one or more of the pyridyl and pyrimidinyl compounds described herein.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

3. Treatment of Diseases of the Central Nervous System (CNS)

In another embodiment, the pyridyl and pyrimidinyl derivatives are used in a method of treating a disease of the central nervous system in a subject in need thereof comprising administering to the subject a therapeutically effective amount of any one or more of the pyridyl and pyrimidinyl compounds described herein.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

Definitions:

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" means that amount of active compound or pharmaceutical agent that elicits the biological or medicinal response in a tissue, system, animal or human that is being sought by a researcher, veterinarian, medical doctor or other clinician. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the compounds are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disease.

Furthermore, in the present invention, when the compounds are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Histone Deacetylases and Histone Deacetylase Inhibitors

As demonstrated herein, the pyridyl and pyrimidinyl derivatives of the present invention show improved activity as histone deacetylase (HDAC) inhibitors. Accordingly, in one embodiment, the invention relates to a method of inhibiting the activity of histone deacetylase comprising contacting the histone deacetylase with an effective amount of one or more of the pyridyl and pyrimidinyl compounds described herein.

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assays which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., J. Natl. Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H]acetyl-labelled murine erythroleukemia cell-derived histone) can be added and the sample can be incubated for 20 minutes at 37° C. in a total volume of 30 μL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIO-MOL Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 μg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the $p21^{WAF1}$ gene. The $p21^{WAF1}$ protein is induced within 2 hours of culture with HDAC inhibitors in a variety of transformed cells using standard methods. The induction of the $p21^{WAF1}$ gene is associated with accumulation of acetylated histones in the chromatin region of this gene. Induction of $p21^{WAF1}$ can therefore be recognized as involved in the G1 cell cycle arrest caused by HDAC inhibitors in transformed cells.

Combination Therapy

The compounds of the present invention can be administered alone or in combination with other therapies suitable for the disease or disorder being treated. Where separate dosage formulations are used, the compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the compound and the other therapeutic agent are realized by the patient at substantially the same time. In an embodiment, such beneficial effect is achieved when the target blood level concentrations of each active drug are maintained at substantially the same time.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, lfulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)

ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP 1, inhibitors of CENP-E, inhibitors of MCAK, inhibitors of Kifl4, inhibitors of Mphosphl and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over IC50 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $E_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WT1, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to anastrozole, letrozole and exemestane.

A compound of the instant invention may also be useful for treating or preventing cancer in combination with siRNA therapeutics.

A compound of the instant invention may also be useful for treating or preventing cancer in combination with compounds which induce terminal differentiation of the neoplastic cells. Suitable differentiation agents include the compounds disclosed in any one or more of the following references.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature* (Lond.) 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The compounds of the instant invention are useful in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®);

porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vinorelbine (Navelbine®); zoledronate (Zometa®); and zoledronic acid (Zometa®).

The use of all of these approaches in combination with the instant compounds described herein are within the scope of the present invention.

Dosages and Dosing Schedules

The dosage regimen utilizing the compounds of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 2-4000 mg administered orally once-daily, twice-daily or three times-daily, continuous (every day) or intermittently (e.g., 3-5 days a week). For example, when used to treat the desired disease, the dose of the compound can range between about 2 mg to about 2000 mg per day.

The compounds of the present invention are administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

Typically, an intravenous formulation may be prepared which contains a concentration of the compound of the invention of between about 1.0 mg/mL to about 10 mg/mL. In one example, a sufficient volume of intravenous formulation can be administered to a patient in a day such that the total dose for the day is between about 1 and about 1500 mg/m$^2$.

Subcutaneous formulations, preferably prepared according to procedures well known in the art at a pH in the range between about 5 and about 12, also include suitable buffers and isotonicity agents, as described below. They can be formulated to deliver a daily dose of HDAC inhibitor in one or more daily subcutaneous administrations, e.g., one, two or three times each day.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

It should be apparent to a person skilled in the art that the various modes of administration, dosages and dosing schedules described herein merely set forth specific embodiments and should not be construed as limiting the broad scope of the invention. Any permutations, variations and combinations of the dosages and dosing schedules are included within the scope of the present invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

Pharmaceutical Compositions

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. In one embodiment, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof In one embodiment, the diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof Furthermore, the compositions of the present invention may be in the form of controlled release or immediate release formulations.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

One can formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The compounds of the present invention may be administered intravenously on the first day of treatment, with oral administration on the second day and all consecutive days thereafter.

The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause unmanageable toxicity in the patient. In the certain embodiments, the amount of the compound that is administered to the patient is less than the amount that causes a concentration of the compound in the patient's plasma to equal or exceed the toxic level of the compound. In one embodiment, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM. In another embodiment, the concentration of the compound in the patient's plasma is maintained at about 100 nM. In another embodiment, the concentration of the compound in the patient's plasma is maintained at about 500 nM. In another embodiment, the concentration of the compound in the patient's plasma is maintained at about 1000 nM. In another embodiment, the concentration of the compound in the patient's plasma is maintained at about 2500 nM. In another embodiment, the concentration of the compound in the patient's plasma is maintained at about 5000 nM. The optimal amount of the compound that should be administered to the patient in the practice of the present invention will depend on the particular compound used and the type of cancer being treated.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

In Vitro Methods:

The present invention also provides methods of using the pyridyl and pyrimidinyl derivatives of the present invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the pyridyl and pyrimidinyl derivatives described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the pyridyl and pyrimidinyl compounds described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the pyridyl and pyrimidinyl compounds described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the pyridyl and pyrimidinyl compounds described herein.

In another embodiment, the invention relates to an in vitro method of inducing terminal differentiation of tumor cells in a tumor comprising contacting the cells with an effective amount of any one or more of the pyridyl and pyrimidinyl compounds described herein.

Although the methods of the present invention can be practiced in vitro, it is contemplated that the preferred embodiment for the methods of selectively inducing terminal differentiation, cell growth arrest and/or apoptosis of neoplastic cells, and of inhibiting HDAC will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the pyridyl and pyrimidinyl derivatives described herein.

In a particular embodiment, the present invention relates to a method of selectively inducing terminal differentiation of neoplastic cells and thereby inhibiting proliferation of such cells in a subject. The method comprises administering to the subject an effective amount of one or more of the pyridyl and pyrimidinyl derivatives described herein.

In another embodiment, the invention relates to a method of selectively inducing cell growth arrest of neoplastic cells and thereby inhibiting proliferation of such cells in a subject. The method comprises administering to the subject an effective amount of one or more of the pyridyl and pyrimidinyl derivatives described herein.

In another embodiment, the invention relates to a method of selectively inducing apoptosis of neoplastic cells and thereby inhibiting proliferation of such cells in a subject. The method comprises administering to the subject an effective amount of one or more of the pyridyl and pyrimidinyl derivatives described herein.

In another embodiment, the invention relates to a method of treating a patient having a tumor characterized by proliferation of neoplastic cells. The method comprises administering to the patient one or more of the pyridyl and pyrimidinyl derivatives described herein. The amount of compound is effective to selectively induce terminal differentiation, induce cell growth arrest and/or induce apoptosis of such neoplastic cells and thereby inhibit their proliferation.

The invention is illustrated in the examples in the Experimental Details Section that follows. This section is set forth to aid in an understanding of the invention but is not intended to, and should not be construed to limit in any way the invention as set forth in the claims which follow thereafter.

EXPERIMENTAL DETAILS SECTION
Example 1
Synthesis
The compounds of the present invention were prepared by the general methods outlined in the synthetic schemes below, as exemplified below.
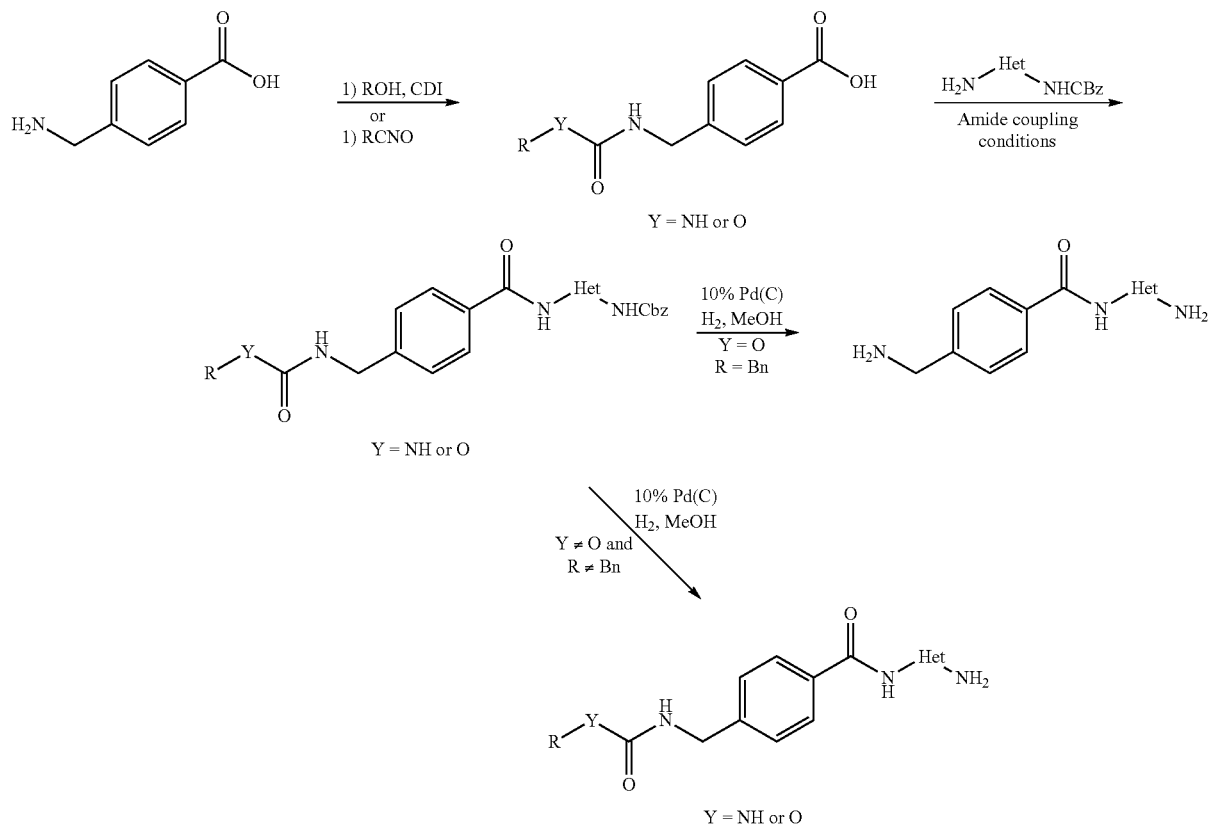
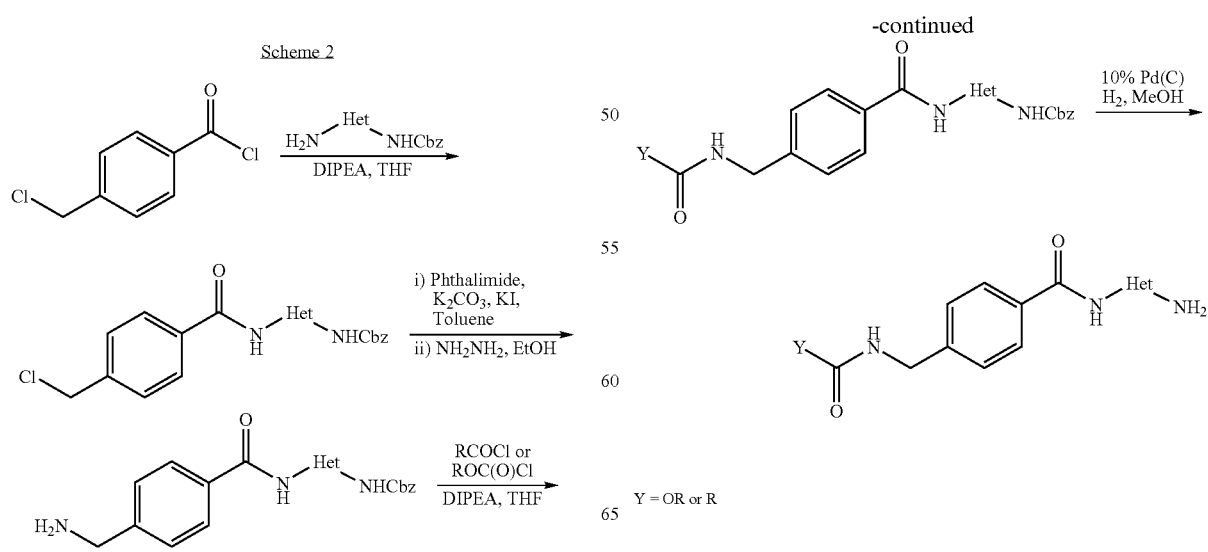

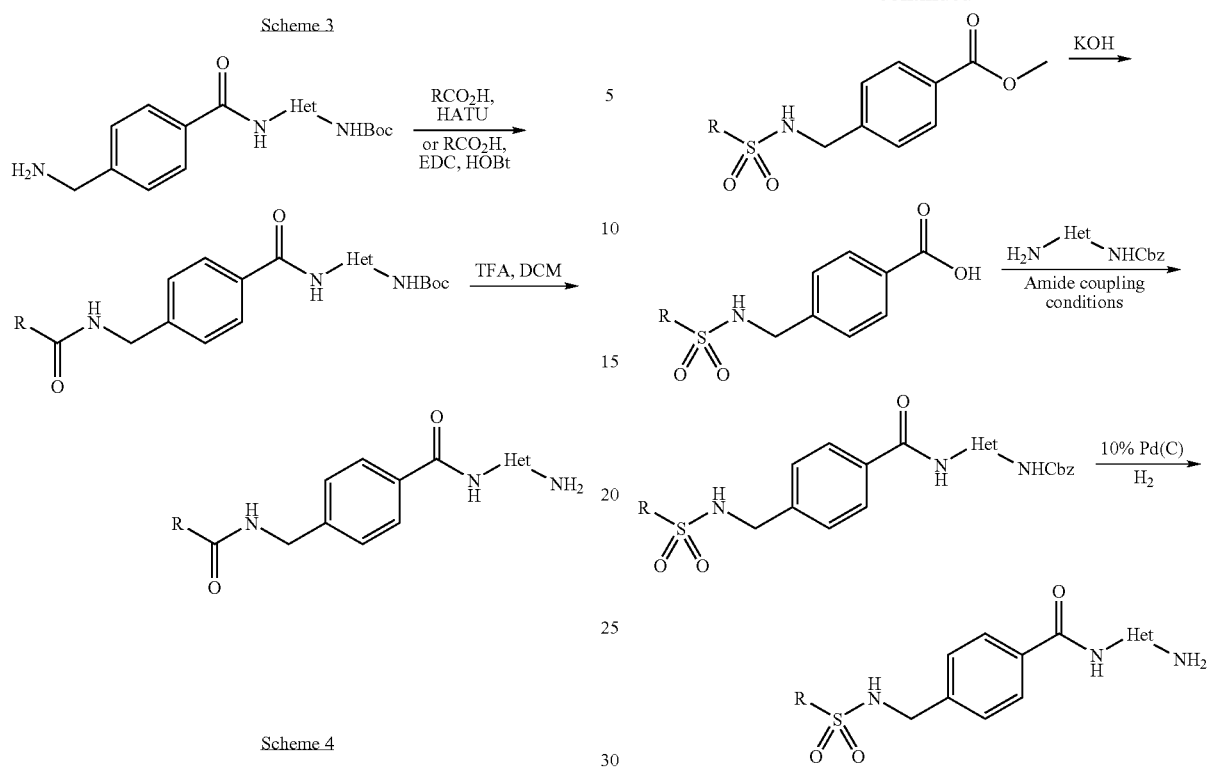
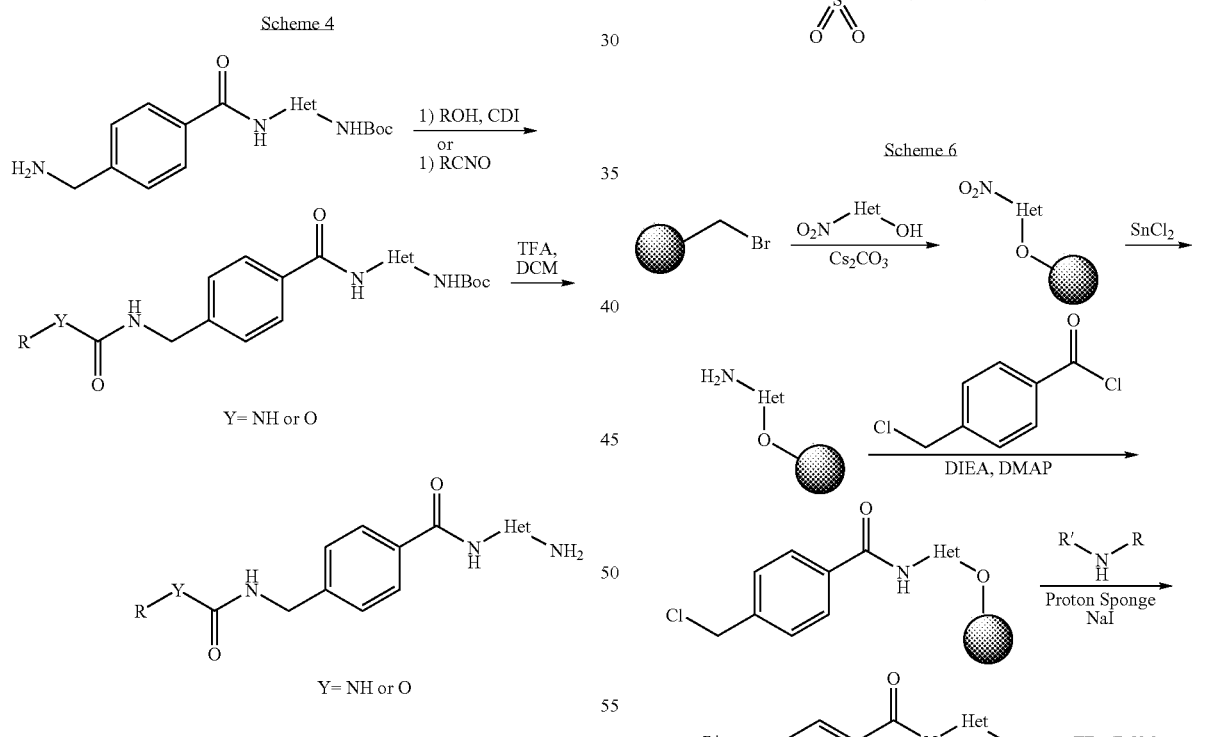
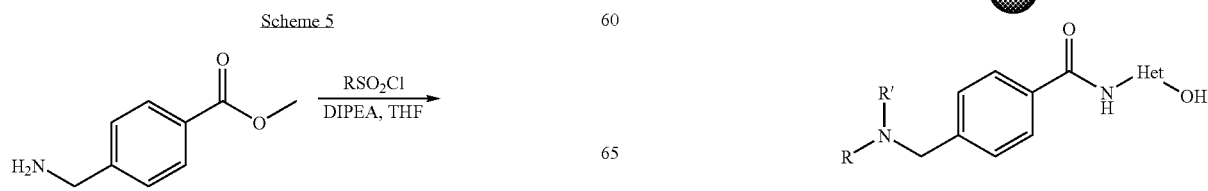

Scheme 7
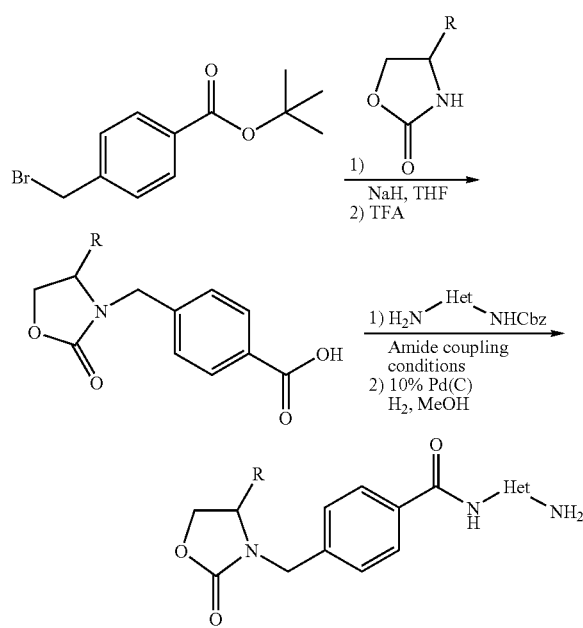
Scheme 8
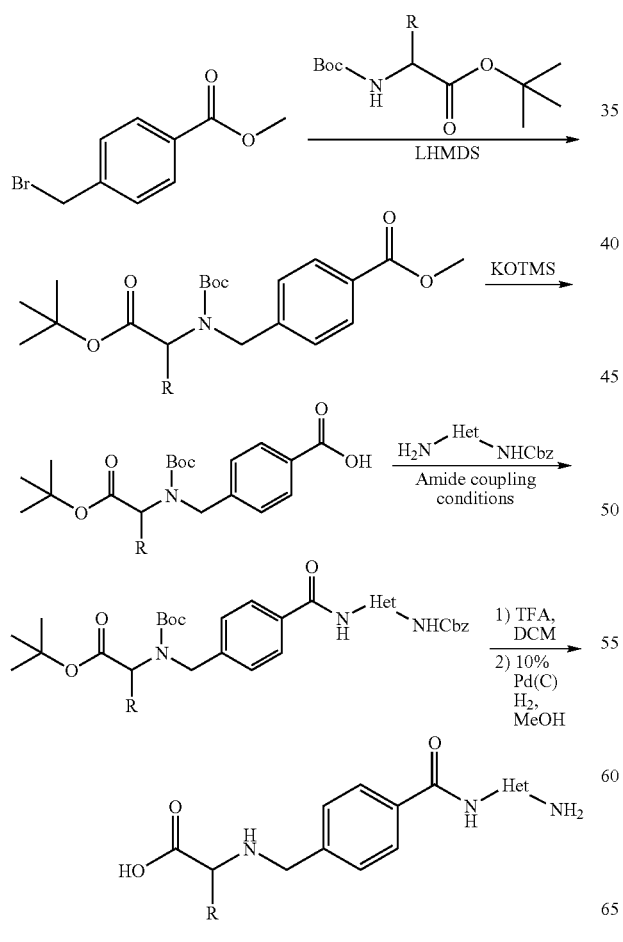
Scheme 9
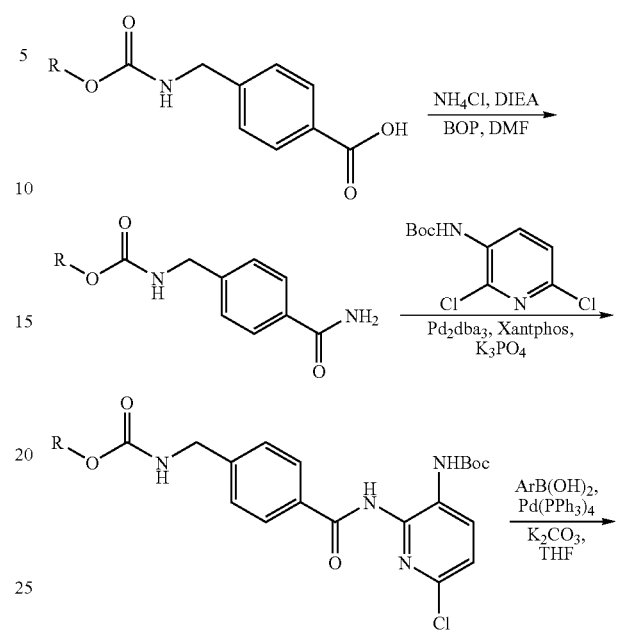
Scheme 10
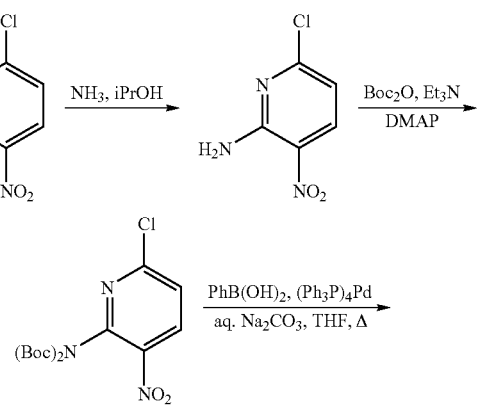

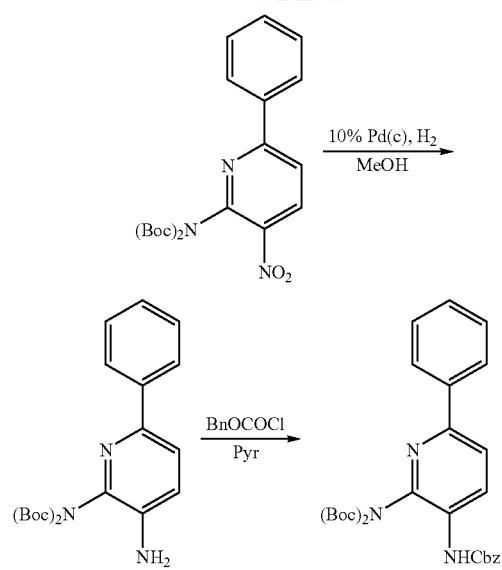
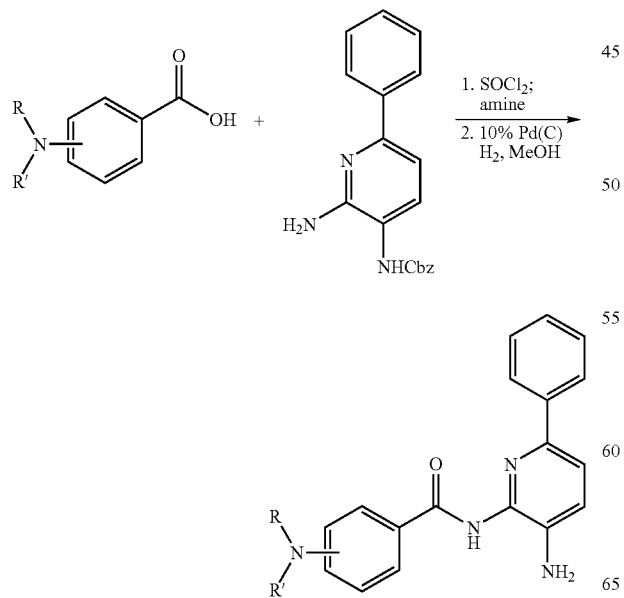
Scheme 12
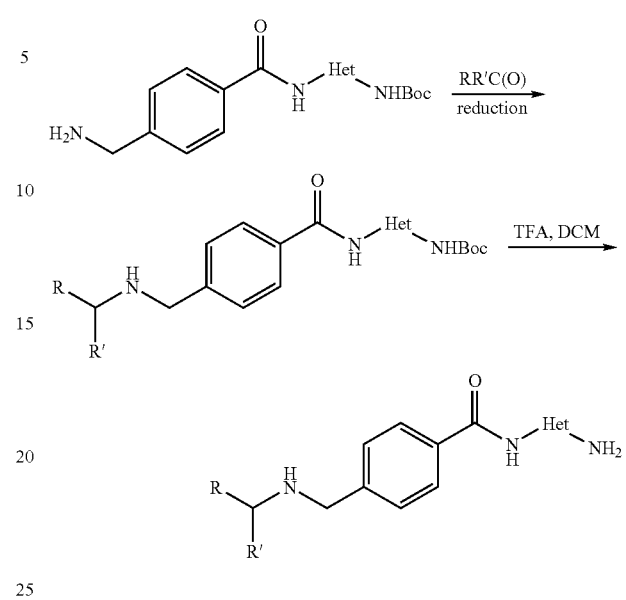
Scheme 13
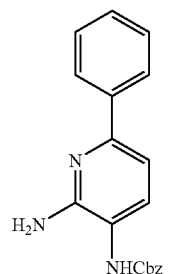
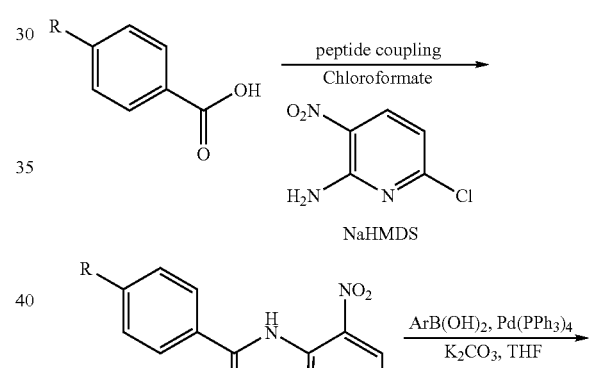
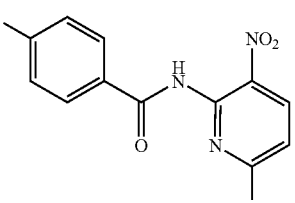
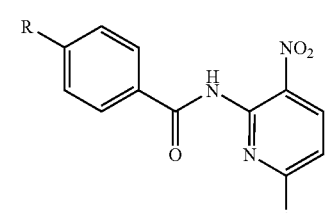
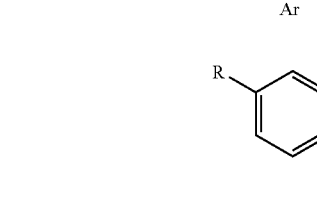
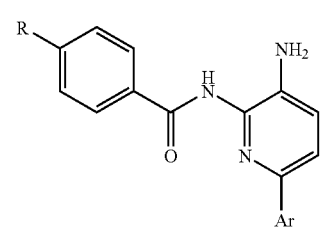

Scheme 14
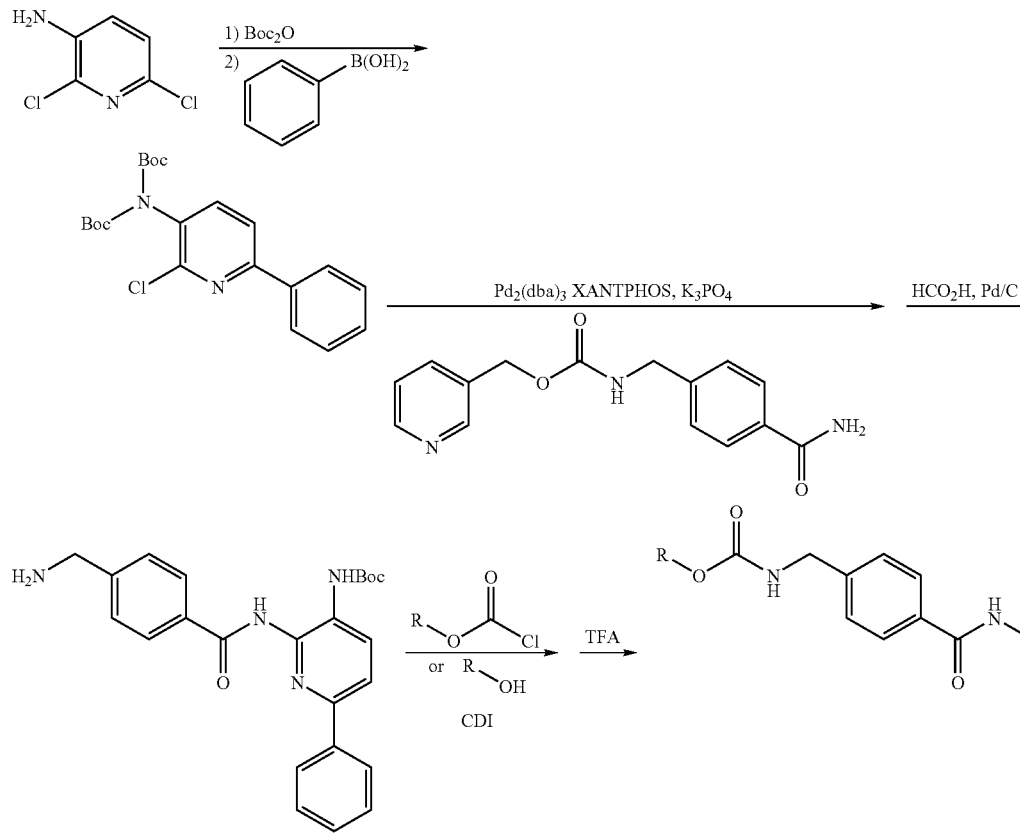
Scheme 15
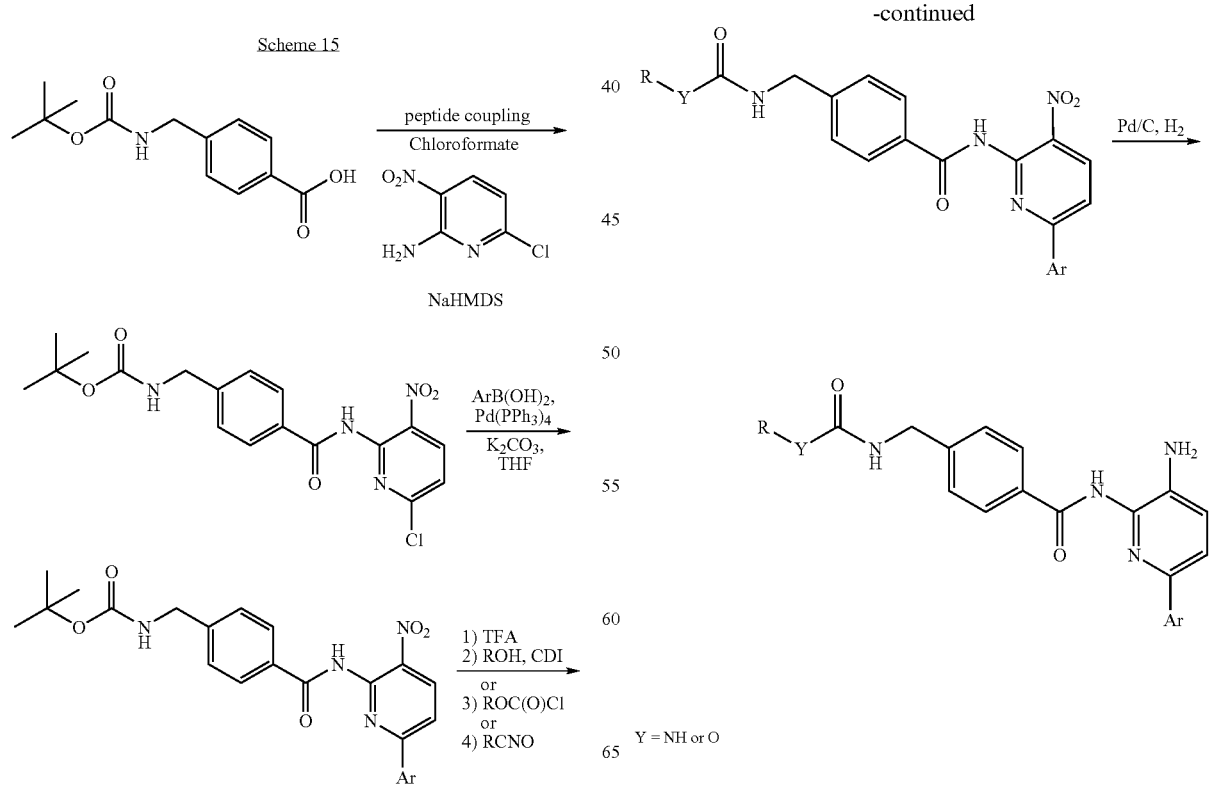
Y = NH or O

Scheme 16

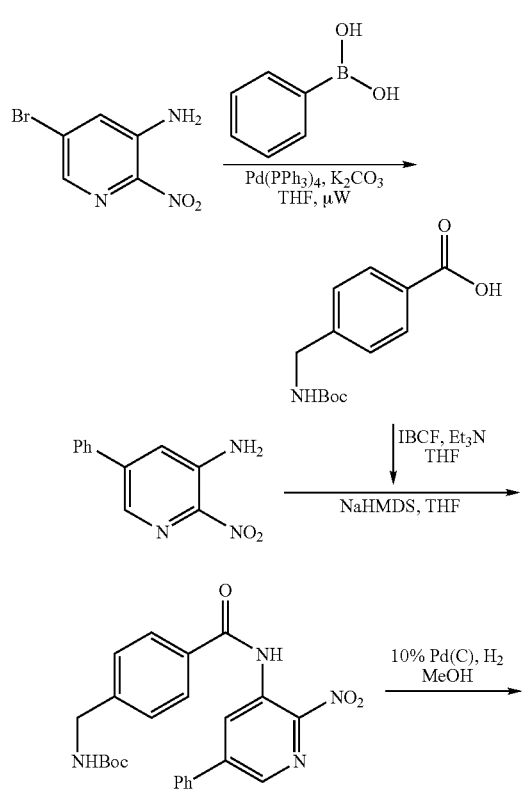

A. Compounds Synthesized According to Scheme 9

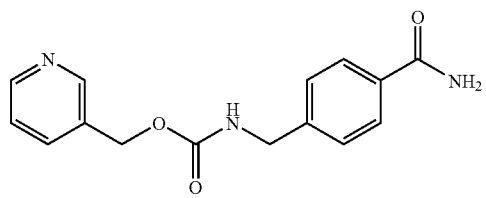 [SMILES: NC(=O)c1ccc(CNC(=O)OCc2cccnc2)cc1]

Pyridin-3-ylmethyl{[4-(aminocarbonyl)phenyl]methyl}carbamate

A solution of 4-({[(pyridin-3-ylmethoxy)carbonyl]amino}methyl)benzoic acid (1.0 g, 3.49 mmol), ammonium chloride (0.47 g, 8.73 mmol) and BOP (2.32 g, 5.24 mmol) in DMF (10 mL) was treated with DIEA (1.13 g. 8.73 mmol) and the resulting solution was stirred at ambient temperature for 16 hours. The reaction mixture was diluted with water (150 mL) and the resulting solids were filtered, washed with additional water and dried in vacuo to give pyridin-3-ylmethyl{[4-(aminocarbonyl)phenyl]methyl}carbamate as a white solid. MS: cal'd 286 (MH+), exp 286 (MH+).

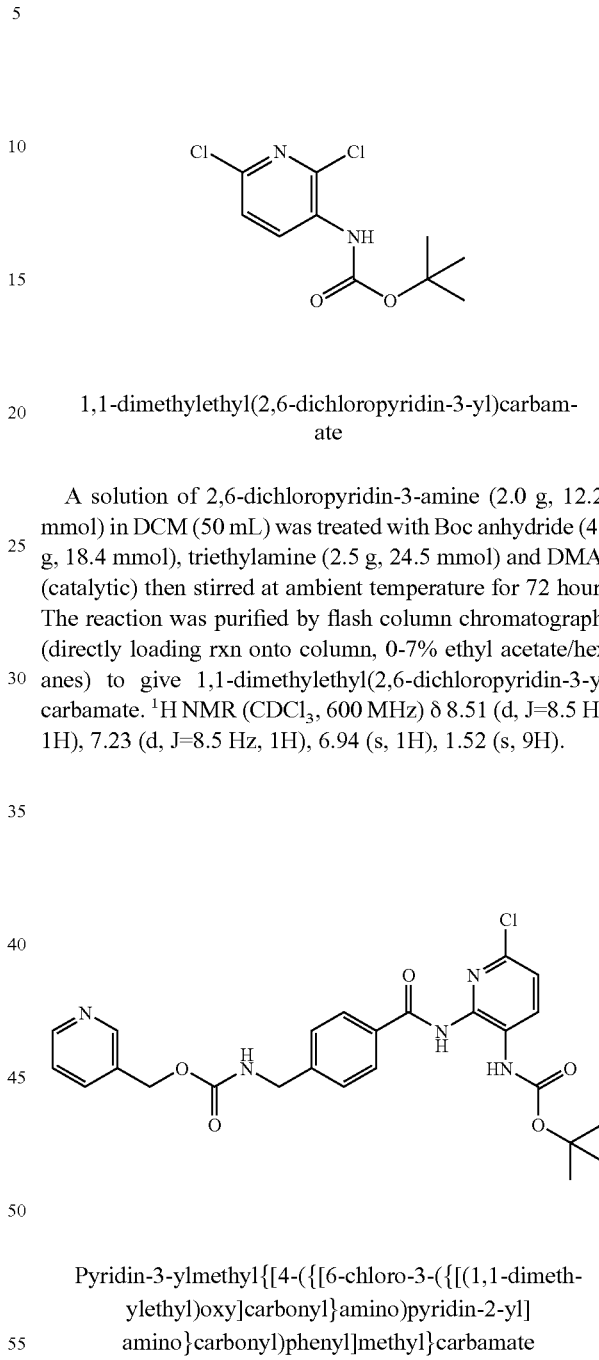

1,1-dimethylethyl(2,6-dichloropyridin-3-yl)carbamate

A solution of 2,6-dichloropyridin-3-amine (2.0 g, 12.27 mmol) in DCM (50 mL) was treated with Boc anhydride (4.0 g, 18.4 mmol), triethylamine (2.5 g, 24.5 mmol) and DMAP (catalytic) then stirred at ambient temperature for 72 hours. The reaction was purified by flash column chromatography (directly loading rxn onto column, 0-7% ethyl acetate/hexanes) to give 1,1-dimethylethyl(2,6-dichloropyridin-3-yl)carbamate. $^1$H NMR (CDCl$_3$, 600 MHz) δ 8.51 (d, J=8.5 Hz, 1H), 7.23 (d, J=8.5 Hz, 1H), 6.94 (s, 1H), 1.52 (s, 9H).

Pyridin-3-ylmethyl{[4-({[6-chloro-3-({[(1,1-dimethylethyl)oxy]carbonyl}amino)pyridin-2-yl]amino}carbonyl)phenyl]methyl}carbamate A solution of pyridin-3-ylmethyl{[4-(aminocarbonyl)phenyl]methyl}carbamate (0.2 g, 0.70 mmol), 1,1-dimethylethyl (2,6-dichloropyridin-3-yl)carbamate (0.18 g, 0.70 mmol), Pd$_2$(dba)$_3$ (32 mg, 0.035 mmol), Xantphos (41 mg, 0.07 mmol) and K$_3$PO$_4$ (0.45 g, 2.1 mmol) in dioxane (3 mL) was degassed with nitrogen, sealed and heated to 100° C. for 14 hours. The reaction was diluted with ethyl acetate (50 mL), filtered through Celite and evaporated in vacuo. Purification by flash chromatography (0-3% methanol/DCM) gave pyri din-3-ylmethyl{[4-({[6-chloro-3-({[(1,1-dimethylethyl)oxy]carbonyl}amino)pyridin-2-yl]amino}carbonyl)phenyl]methyl}carbamate. MS: cal'd 512 (MH⁺), exp 512 (MH⁺).

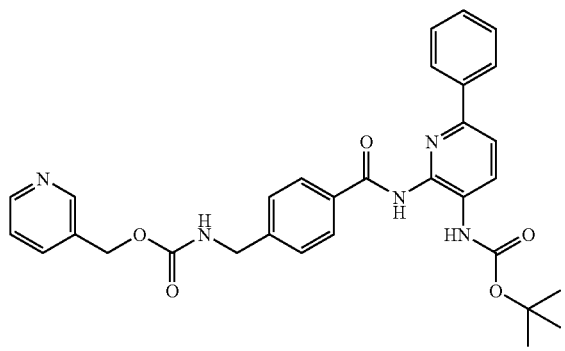 [SMILES: CC(C)(C)OC(=O)Nc1ccc(-c2ccccc2)nc1NC(=O)c1ccc(CNC(=O)OCc2cccnc2)cc1]

1,1-dimethylethyl{6-phenyl-2-[({4-[({[(pyridin-3-ylmethyl)oxy]carbonyl}amino)methyl]phenyl}carbonyl)amino]pyridin-3-yl}carbamate A solution of pyridin-3-ylmethyl{[4-({[6-chloro-3-({[(1,1-dimethylethyl)oxy]carbonyl}amino)pyridin-2-yl]amino}carbonyl)phenyl]methyl}carbamate (0.1 g, 0.195 mmol), phenyl boronic acid (29 mg, 0.24 mmol), Pd(PPh₃)₄ (12 mg, 0.01 mmol) and K₂CO₃ (54 mg, 0.39 mmol) in THF (3 mL) was degassed with nitrogen, sealed and heated to 120° C. in the microwave for 20 minutes. The reaction was loaded directly onto a silica cartridge, dried and purified by flash column chromatography (2-4% methanol/DCM) to give 1,1-dimethylethyl{6-phenyl-2-[({4-[({[(pyridin-3-ylmethyl)oxy]carbonyl}amino)methyl]phenyl}carbonyl)amino]pyridin-3-yl}carbamate. MS: cal'd 554 (MH⁺), exp 554 (MH⁺).

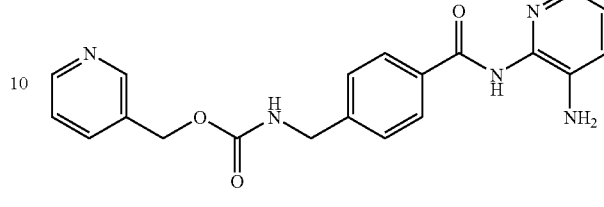

Pyridin-3-ylmethyl[(4-{[(3-amino-6-phenylpyridin-2-yl)amino]carbonyl}phenyl)methyl]carbamate A solution of 1,1-dimethylethyl{6-phenyl-2-[({4-[({[(pyridin-3-ylmethyl)oxy]carbonyl}amino)methyl]phenyl}carbonyl)amino]pyridin-3-yl}carbamate (25 mg, 0.045 mmol) in ethyl acetate (5 mL) was treated with 4M HCl in dioxane (1.13 mL, 4.52 mmol) and stirred at ambient temperature for 16 hours. The reaction was evaporated in vacuo and purified by flash column chromatography (0-5% methanol(w/1% ammonia)/DCM) to give pyridin-3-ylmethyl[(4-{[(3-amino-6-phenylpyridin-2-yl)amino]carbonyl}phenyl)methyl]carbamate. ¹H NMR (CD₃OD, 600 MHz) δ 8.58 (br s, 1H), 8.49 (br s, 1H), 8.00 (d, J=8.21 Hz, 2H), 7.89 (d, J=7.63 Hz, 3H), 7.75 (t, J=5.87 Hz, 1H), 7.61 (d, J=8.21 Hz, 1H), 7.58 (d, J=6.75 Hz, 1H), 7.38 (m, 8H), 5.18 (s, 2H), 4.38 (d, J=5.87 Hz, 2H). MS: cal'd 454 (MH⁺), exp 454 (MH⁺). The in vitro HDAC1 IC₅₀ of this compound is 84 nM. The IC₅₀ of this compound in HCT-116 cells is 580 nM. Percent Cyp inhibitions at 10 μM are 46, 54 and 55%, for Cyp3A4, 2C9, and 2D6, respectively. The inflection point for MK-499 binding is >30 μM.

Additional analogs were prepared in procedures similar to those described for the preparation of the above.

TABLE 1

| Structure | Name | MS | Salt forms |
|---|---|---|---|
| 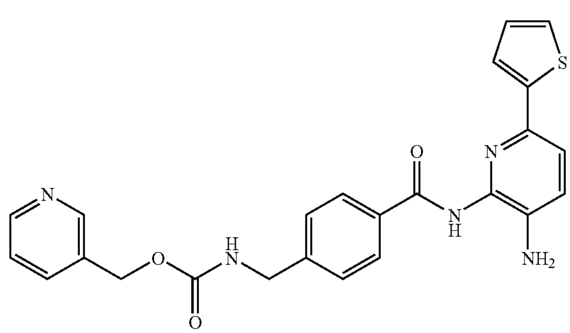 [SMILES: Nc1ccc(-c2cccs2)nc1NC(=O)c1ccc(CNC(=O)OCc2cccnc2)cc1] | pyridin-3-ylmethyl {[4-({[3-amino-6-(2-thienyl)pyridin-2-yl]amino}carbonyl)phenyl]methyl}carbamate | cal'd 460 (MH⁺), exp 460 (MH⁺) | Free base |

The in vitro HDAC1 IC$_{50}$ of the compound in Table 1 is 56 nM. The IC$_{50}$ of this compound in HCT-116 cells is 560 nM.

B. Procedure for Making the Protected Pyridyl Warhead in Scheme 10

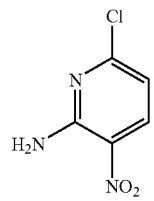 [SMILES: Nc1nc(Cl)ccc1[N+](=O)[O-]]

6-Chloro-3-nitropyridin-2-amine

Procedure obtained from the Journal of Labeled Compounds and Radiopharmaceuticals, 1987, 24, 1-14. A suspension of 2,6-dichloro-3-nitropyridine (25.2 g, 131 mmol) and isopropanol (1.74 l) was temperature-stabilized with a rt water bath and ammonia was bubbled through the stirred solution for 16 h. The reaction was concentrated to a residue and taken into Et$_2$O and THF (1:1, 1l). Water (400 mL) was added, and the solution made basic via the addition of 5N aq. NaOH. The organic layer was separated, dried (MgSO$_4$) and concentrated to afford an orange solid recrystallized from hot 95% EtOH to afford the requisite product as yellow needles. $^1$H NMR (DMSO-d6, 600 MHz) d 8.35 (d, J=8.5 Hz, 1H), 8.22 (br s, 2H), 6.73 (d, J=8.5 Hz, 1H).

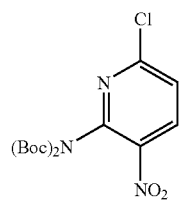

Di-tert-butyl(6-chloro-3-nitropyridin-2-yl)imidodicarbonate

A suspension of 6-chloro-3-nitropyridin-2-amine (7.08 g, 40.8 mmol), dichloromethane (122 mL) and acetonitrile (122 mL) was treated with Boc$_2$O (21.4 g, 97.9 mmol) and triethylamine (22.7 mL, 163 mmol). A crystal of DMAP was added and the orange suspension became homogenous and was stirred for 16 h. The reaction was concentrated to a brown oil which was taken into EtOAc and washed with 1M aq. HCl 2×, sat. aq. NaHCO$_3$, brine, dried (MgSO$_4$) and concentrated to afford a brown residue purified via MPLC, silica cartridge, 50-80% methylene chloride in heptanes to afford the product as a light tan solid. $^1$H NMR (DMSO-d6, 600 MHz) d 8.67 (d, J=8.5 Hz, 1H), 7.90 (d, J=8.5 Hz, 1H), 1.34 (s, 19H); MS cal'd 396 (M+Na)$^+$, exp 396 (M+Na)$^+$.

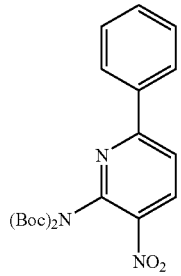

Di-tert-butyl(3-nitro-6-phenylpyridin-2-yl)imidodicarbonate

A mixture of di-tert-butyl(6-chloro-3-nitropyridin-2-yl)imidodicarbonate (700 mg, 1.87 mmol), phenylboronic acid (274 mg, 2.25 mmol) and tetrakistriphenylphosphine palladium (217 mg, 0.187 mmol) were blanketed with argon and taken up in THF (15.0 mL) and 2M aq. Na$_2$CO$_3$ (3.74 mL). The suspension was purged with bubbling argon for 20 min, then the reaction was sealed and heated via microwave to 120° C. for 2 h. The reaction was cooled, diluted with EtOAc and filtered through celite. The filtrate was washed with water, brine, dried (MgSO$_4$) and concentrated to afford material purified via MPLC, silica cartridge, 5-20% EtOAc in heptanes to afford the product as a light yellow solid. $^1$H NMR (DMSO-d6, 600 MHz) d 8.68 (d, J=8.5 Hz, 1H), 8.29 (d, J=8.5 Hz, 1H), 8.16-8.12 (m, 2H), 7.57-7.54 (m, 3H), 1.35 (s, 18H); MS cal'd 438 (M+Na)$^+$, exp 438 (M+Na)$^+$.

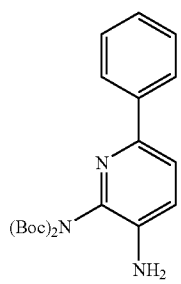

Di-tert-butyl(3-amino-6-phenylpyridin-2-yl)imidodicarbonate

A solution of di-tert-butyl(3-nitro-6-phenylpyridin-2-yl)imidodicarbonate (378 mg, 0.910 mmol) and MeOH (18.1 mL) was treated with 10% palladium on carbon (~20 mg) and fitted with a hydrogen balloon. After 30 min the reaction was filtered through celite and concentrated to afford a residue which was used in the next reaction without purification. MS cal'd 386 (M+H)$^+$, exp 386 (M+H)$^+$.

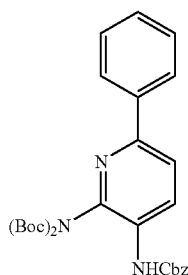

Di-tert-butyl(3-{[(benzyloxy)carbonyl]amino}-6-phenylpyridin-2-yl)imidodicarbonate A solution of di-tert-butyl(3-amino-6-phenylpyridin-2-yl) imidodicarbonate (351 mg, 0.910 mmol, theoretical yield from previous reaction), THF (1.82 mL) and methylene chloride (1.82 mL) was cooled 0° C. and pyridine (0.294 mL, 3.64 mmol) and benzyl chloroformate (0.256 mL, 1.82 mmol) were added dropwise. The reaction was stirred for 2 h, diluted with EtOAc and washed with 1M aq. HCl2×, sat. aq. NaHCO$_3$, brine, dried (MgSO$_4$) and concentrated to afford a residue purified via MPLC, silica cartridge, 5-20% EtOAc in heptanes to afford the product as a clear light orange oil. MS cal'd 520 (M+H)$^+$, exp 520 (M+H)$^+$.

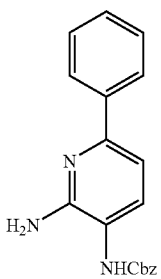

Benzyl(2-amino-6-phenylpyridin-3-yl)carbamate

A solution of di-tert-butyl(3-{[(benzyloxy)carbonyl] amino}-6-phenylpyridin-2-yl)imidodicarbonate (359 mg, 0.691 mmol) and methylene chloride (2.76 mL) was treated with TFA (0.691 mL) in one portion. The reaction was stirred for 3 h, then concentrated via rotovap slowly to afford a residue purified via MPLC, silica cartridge, 0-5% MeOH in methylene chloride to afford the product as a light orange solid. $^1$H NMR (DMSO-d6, 600 MHz, rotamers present) δ 9.04 (br s, 1H), 7.86 (d, J=7.3 Hz, 1H), 7.47-7.30 (m, 5H), 7.15 (d, J=8.2 Hz, 1H), 6.40 (br s, 2H), 5.16 (s, 2H); MS cal'd 320 (M+H)$^+$, exp 320 (M+H)$^+$.

C. Procedure to Prepare Analogues Described in Scheme 11

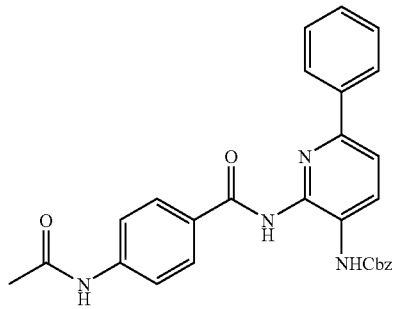 [SMILES: CC(=O)Nc1ccc(C(=O)Nc2nc(-c3ccccc3)ccc2NC(=O)OCc2ccccc2)cc1]

Benzyl(2-{[4-(acetylamino)benzoyl]amino}-6-phenylpyridin-3-yl)carbamate

A solution of 4-(acetylamino)benzoic acid (33.6 mg, 0.188 mmol) and methylene chloride (0.190 mL) was cooled to 0° C. and treated with thionyl chloride (41 uL, 0.563 mmol) and a drop of DMF. The cold bath was removed, and the reaction progress was checked via piperidine quench and LCMS. The reaction was thoroughly concentrated and dissolved in methylene chloride:THF (1:1, 0.240 mL) and benzyl(2-amino-6-phenylpyridin-3-yl)carbamate (20 mg, 0.0626 mmol) added. After 2 days the reaction was concentrated, taken into DMF and purified via reversed phase HPLC, 20-80% MeCN in water with 0.05% TFA to afford the requisite compound which was taken to the next reaction. MS cal'd 481 (M+H)$^+$, exp 481 (M+H)$^+$.

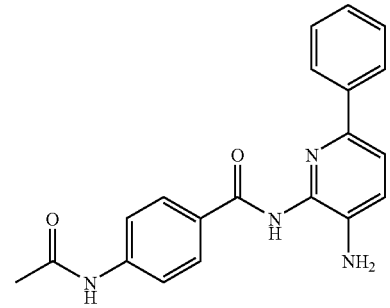 [SMILES: CC(=O)Nc1ccc(C(=O)Nc2nc(-c3ccccc3)ccc2N)cc1]

4-(Acetylamino)-N-(3-amino-6-phenylpyridin-2-yl) benzamide

A solution of benzyl(2-{[4-(acetylamino)benzoyl] amino}-6-phenylpyridin-3-yl)carbamate from the previous step (30 mg theoretical, 0.0626 mmol) and MeOH (100 uL) were treated with 10% palladium on carbon (cat) and the reaction was fitted with a hydrogen balloon. After one hour the reaction was diluted with EtOAc, filtered through celite and concentrated to a residue purified via reversed phase HPLC (30-70% MeCN in water with 0.05% TFA) to afford fractions concentrated via sublimation to afford the title compound as a light yellow solid and a TFA salt. $^1$H NMR (MeOH-d4, 600 MHz) δ 8.04 (d, J=8.8 Hz, 2H), 7.87 (d, J=7.3 Hz, 2H), 7.76 (t, 8.2 Hz, 3H), 7.62 (d, J=8.5 Hz, 1H), 7.51 (t, J=7.6 Hz, 2H), 7.45 (d, J=7.3 Hz, 1H), 2.18 (s, 3H); MS cal'd (M+H)$^+$, exp 347 (M+H)$^+$. The in vitro HDAC1 IC$_{50}$ of this compound is 86 nM. The IC$_{50}$ of this compound in HCT-116 cells is 2050 nM.

Additional analogs were prepared in procedures similar to those described for the preparation of the above.

TABLE 2

| Structure | Name | MS | Salt forms | HDAC1 IP* (nM) | Prol-72 hr IP* (μM) |
|---|---|---|---|---|---|
| 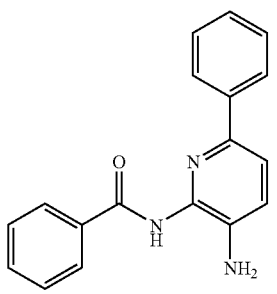 [SMILES: Nc1ccc(-c2ccccc2)nc1NC(=O)c1ccccc1] | N-(3-amino-6-phenylpyridin-2-yl)benzamide | cal'd 290 (MH$^+$), exp 290, (MH$^+$) | Free base | 1155 | nd |
| 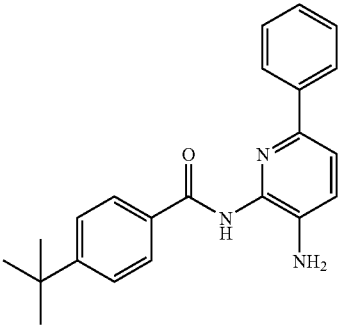 [SMILES: CC(C)(C)c1ccc(C(=O)Nc2nc(-c3ccccc3)ccc2N)cc1] | N-(3-amino-6-phenyl-2-pyridinyl)-4-(1,1-dimethylethyl) benzamide | cal'd 346 (MH$^+$), exp 346 (MH$^+$) | Free base | 235 | 20 |
| 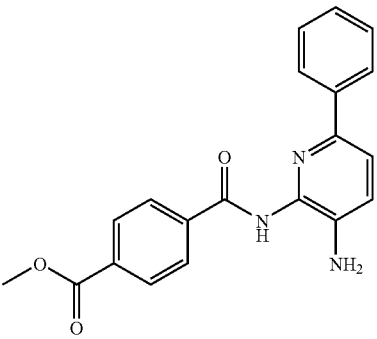 [SMILES: COC(=O)c1ccc(C(=O)Nc2nc(-c3ccccc3)ccc2N)cc1] | benzoic acid, methyl 4-[[(3-amino-6-phenyl-2-pyridinyl)amino] carbonyl]benzoate | cal'd 348 (MH$^+$), exp 348 (MH$^+$). | Free base | 195 | 20 |

*IP = inflection point

^nd = not determined

D. Compounds Synthesized According to Scheme 13

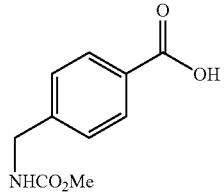

4-Carbomethoxyaminomethyl benzoic acid

To suspension of the 4-aminomethylbenzoic acid (10 g, 66.2 mmol) in 1,4-dioxane (100 mL) were added methyl chloroformate (5.4 mL, 69.5 mmol) and dimethyl acetamide (3.4 mL). The reaction mixture was then heated to 65° C. overnight. Reaction mixture was evaporated to dryness and the residue was triturated with water. The solids were filtered and dried to give pure product as white solid. $^1$H NMR (600 MHz, DMSO) δ 12.84 (bs, 1H), 7.85 (d, J=7.8 Hz, 2H), 7.73 (t, J=6 Hz, 1H), 7.32 (d, J=7.8 Hz, 2H), 4.20 (bd, J=6 Hz, 2H), 3.52 (s, 3H); MS: (MH$^+$), (MH$^+$).

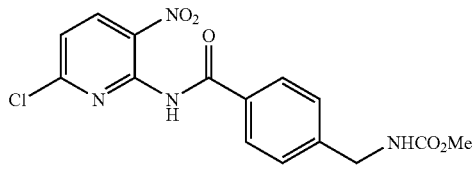

Methyl(4-{[(6-chloro-3-nitropyridin-2-yl)amino]carbonyl}benzyl)carbamate

To suspension of 4-carbomethoxyaminomethyl benzoic acid (11.2 g, 53.4 mmol) in anhydrous THF (300 mL) was added TEA (14.9 mL, 107 mmol) and stirred at RT until most of the acid goes into solution. To this solution then was added isobutyl chloroformate (7.0 mL, 53.4 mmol) and the resulting suspension was stirred at RT for 2.5 h. After this time the reaction filtered under N$_2$ atmosphere through a sintered glass frit to give a clear solution of mixed anhydride in THF, which was then added to sodium salt of amine. To a solution of 2-amino-3-nitro-6-chloropyridine (11.6 g, 66.7 mmol) in anhydrous THF (550 mL) was cooled to −10° C. in acetone-ice bath for about 10 min. Then to this yellow solution was added a solution of NaHMDS in THF (1 M, 66.7 mmol) slowly drop wise. During this the reaction become dark orange red, this solution was stirred at −10° C. for 30 min. To the dark red solution of the sodium salt of amine at −10° C. was added the clear solution of mixed anhydride formed above. After the addition the reaction mixture forms a gel kind of appearance, cooling bath was removed and reaction was allowed to proceed at RT for 3 h. The reaction was quenched by addition 1N HCl (400 mL) solution in water and organic layer was separated and aqueous layer was extracted with EtOAc (2×). The combined organic layer was washed with saturated NaHCO$_3$ and brine. Finally the organic layer was dried over anhydrous Na$_2$SO$_4$, concentrated and chromatographed over silica gel EtOAC/Hex (30-100%) to give desired product. $^1$H NMR (600 MHz, CDCl$_3$) δ 10.64 (bs, 1H), 8.45 (d, J=8.4 Hz, 1H), 7.94 (d, J=7.8 Hz, 2H), 7.44 (bd, J=8.4 Hz, 2H), 7.22 (d, J=8.4 Hz, 1H), 5.01 (bs, 1H), 4.45 (bd, J=6.6 Hz, 2H), 3.71 (s, 3H); MS: 365.0 (MH$^+$), 365.0 (MH$^+$).

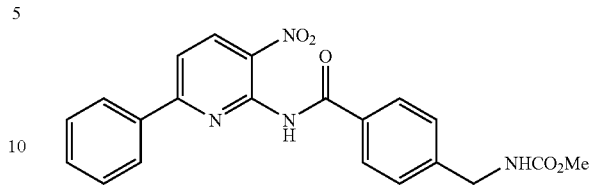

Methyl(4-{[(6-chloro-3-nitropyridin-2-yl)amino]carbonyl}benzyl)carbamate

To methyl(4-{[(6-chloro-3-nitropyridin-2-yl)amino]carbonyl}benzyl)carbamate (12.5 g, 34.3 mmol) in a dry rb-flask were added phenylboronic acid (10.5 g, 86 mmol), K$_2$CO$_3$ (14.2 g, 103 mmol) and Pd(PPh$_3$)$_4$ (1.98 g, 1.71 mmol) and the reaction flask was evacuated and flushed with N$_2$ four times. To this solid reaction mixture was added anhydrous THF (140 mL) and the reaction mixture was degassed by applying vacuum and flushing with N$_2$ five times. The reaction mixture was then heated to reflux overnight. After this time, LC/MS analysis of the reaction mixture should essentially show the desired product. Reaction mixture was concentrated in vacuo and to the residue was added MeOH and stirred for 30 min. All the solids were collected by filtration and washed thoroughly with MeOH and water. The product from this isolation was essentially pure and used in the next step as such. $^1$H NMR (600 MHz, CDCl$_3$) δ 10.92 (bs, 1H), 8.59 (d, J=8.4 Hz, 1H), 8.16 (dd, J=7.7 Hz, 3.6 Hz, 2H), 7.98 (d, J=8.4 Hz, 2H), 7.65 (d, J=8.4 Hz, 1H), 7.50 (m, 3H), 7.45 (m, 2H), 5.13 (bs, 1H), 4.45 (bd, J=6 Hz, 2H), 3.71 (s, 3H); MS: 407.1 (MH$^+$), 407.1 (MH$^+$).

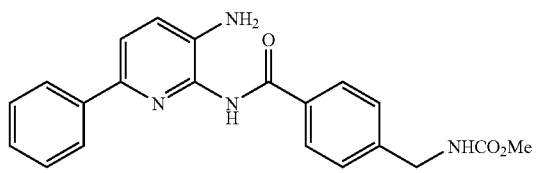

Methyl(4-{[(3-amino-6-phenylpyridin-2-yl)amino]carbonyl}benzyl)carbamate

To a suspension of methyl(4-{[(6-chloro-3-nitropyridin-2-yl)amino]carbonyl}benzyl)carbamate (1.4 g, 3.44 mmol) in MeOH (20 mL) was added Pd on carbon (~500 mg) and the reaction flask was thoroughly flushed with H$_2$. The reaction was then allowed to proceed at RT under a H$_2$ balloon. During the course of reaction, the mixture becomes a homogenous solution. The reaction mixture was filtered through a silica gel pad and the silica gel was washed thoroughly with MeOH. The MeOH layer was concentrated and residue was chromatographed over silica gel to give pure amine as an off-white solid. $^1$H NMR (600 MHz, DMSO) δ 10.37 (bs, 1H), 7.98 (d, J=8.4 Hz, 2H), 7.91 (d, J=7.8 Hz, 2H), 7.75 (t, J=6 Hz, 1H), 7.65 (d, J=8.4 Hz, 1H), 7.36 (m, 4H), 7.26 (d, J=7.8 Hz, 1H), 7.23 (d, J=8.4 Hz, 1H), 5.13 (bs, 2H), 4.23 (bd, J=6 Hz, 2H), 3.53 (s, 3H); MS: 377.1 (MH$^+$), 377.1 (MH$^+$). The in vitro HDAC1 IC$_{50}$ of is 37 nM. The IC$_{50}$ of this compound in HCT-116 cells is 1200 nM. Percent Cyp inhibitions at 10 μM are 29, 49 and 27%, for Cyp3A4, 2C9, and 2D6, respectively. The inflection MK-499 binding is >10 μM.

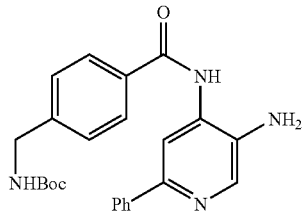 [SMILES: CC(C)(C)OC(=O)NCc1ccc(C(=O)Nc2cc(-c3ccccc3)ncc2N)cc1]

tert-Butyl(4-{[(3-amino-6-phenylpyridin-4-yl)amino]carbonyl}benzyl)carbamate

To a suspension of tert-butyl(4-{[(3-nitro-6-phenylpyridin-4-yl)amino]carbonyl}benzyl)carbamate (30 mg, 0.067 mmoll) in MeOH (2 mL) was added Pd on carbon (~10 mg) and the reaction flask was thoroughly flushed with H$_2$. The reaction was then allowed to proceed at RT under a H$_2$ balloon. During the course of reaction, the mixture becomes a homogenous solution. The reaction mixture was filtered through a silica gel pad and the silica gel was washed thoroughly with MeOH. The MeOH layer was concentrated and residue was purified by HPLC. $^1$H NMR (600 MHz. d$_6$-DMSO) δ 9.78 (s, 1H), 8.15 (s, 1H), 7.96 (s, 1H), 7.91 (d, J=7.8 Hz, 2H), 7.87 (dd, J=8.4, 1.2 Hz, 2H), 7.48 (t, J=6 Hz, 1H), 7.37 (m, 4H), 7.27 (m, 1H), 5.32 (bs, 2H), 4.17 (d, J=6 Hz, 2H), 1.37 (s, 9H); MS: cal'd 419 (M+H)$^+$, exp 419 (M+H)$^+$.

E. Compounds Synthesized According to Scheme 14

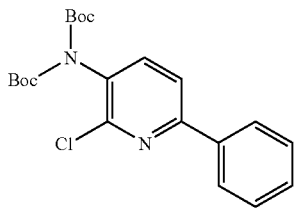 [SMILES: CC(C)(C)OC(=O)N(C(=O)OC(C)(C)C)c1ccc(-c2ccccc2)nc1Cl]

Di-tert-butyl(2-chloro-6-phenylpyridin-3-yl)imidodicarbonate 2,6-dichloropyridin-3-amine (9.39 g, 57.6 mmol), di-tert-butyldicarbonate (503 g, 230 mmol), DMAP (0.704 g, 5.76 mmol) and triethylamine (16.06 mL, 115 mmol) were combined in DCM (230 mL) and stirred at RT overnight. The solvent was evaporated and the residue was triturated with acetonitrile and filtered to provide di-tert-butyl(2,6-dichloropyridin-3-yl)imidodicarbonate. Di-tert-butyl(2,6-dichloropyridin-3-yl)imidodicarbonate (27.7 g, 76 mmol), phenyl boronic acid (13.95, 114 mmol) and sodium carbonate (114 mL, 229 mmol, 2M) were combined with dioxane (692 ml) and DMF (46 ml). The solution was purged with N$_2$ for 20 min. Tetrakis(triphenylphosphine)palladium(0) (4.41 g, 3.81 mmol) was added and reaction heated to 85° C. for 3 h, then cooled to RT and stirred overnight. Reaction was poured into H$_2$O (100 ml) and extracted with EtOAc (2×100) ml. The combined organics were washed with brine and dried over Na$_2$SO$_4$. Crude product was purified by flash chromatography on ISCO 330 g column. (0-20% EtOAc/Heptane). Major spot (TLC 10:1 Heptane/EtOAc) isolated to give 12.06 g of di-tert-butyl(2-chloro-6-phenylpyridin-3-yl)imidodicarbonate as a white solid. $^1$H NMR (CDCl$_3$) δ 8.01 (d, J=7.0 Hz, 2H), 7.69 (d, J=8.1 Hz, 1H), 7.58 (d, J=8.1 Hz, 1H), 7.41-7.48 (m, 3H), 1.40 (s, 18H); MS: cal'd 405 (MH+), exp 405 (MH+).

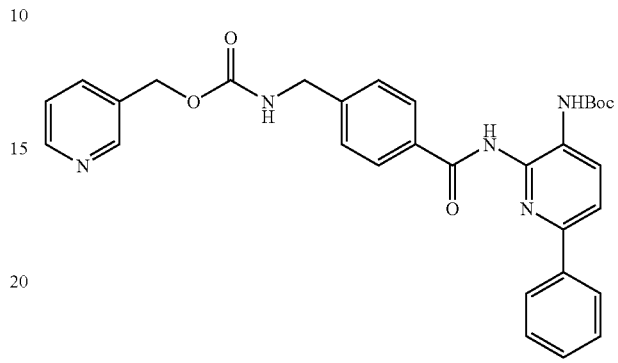

Pyridin-3-ylmethyl{4-[({3-[(tert-butoxycarbonyl)amino]-6-phenylpyridin-2-yl}amino)carbonyl]benzyl}carbamate Pyridin-3-ylmethyl [4-(aminocarbonyl)benzyl]carbamate (0.35 g, 1.24 mmol), di-tert-butyl(2-chloro-6-phenylpyridin-3-yl)imidodicarbonate (0.5 g, 1.24 mmol), Xanthphos (0.07 g, 0.12 mmol), potassium phosphate, tribasic (0.79 g, 3.70 mmol), and Pd$_2$(dba)$_3$ (0.57 g, 0.06 mmol) were combined in a 20 mL microwave vial and dioxane was added. The mixture was degassed for 20 mins, then sealed and heated to 100° C. overnight. Reaction was not complete and was continued another 24 h, for a total of 48 h at 100° C. The reaction was cooled to RT, diluted with saturated NaHCO$_3$ solution and EtOAc, and the layers were separated. The water layer was extracted with EtOAc (2×100 mL). The combined organic fractions were washed with brine, dried over Na$_2$SO$_4$, filtered, and evaporated in vacuo. The residue was purified on a Biotage 65i column to yield pyridin-3-ylmethyl{4-[({3-[(tert-butoxycarbonyl)amino]-6-phenylpyridin-2-yl}amino)carbonyl]benzyl}carbamate. MS: cal'd 554 (MH+), exp 554 (MH+).

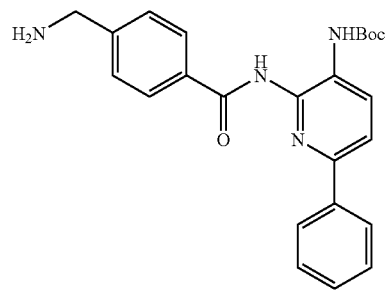 [SMILES: CC(C)(C)OC(=O)Nc1ccc(-c2ccccc2)nc1NC(=O)c1ccc(CN)cc1]

Tert-butyl(2-{[4-(aminomethyl)benzoyl]amino}-6-phenylpyridin-3-yl)carbamate pyridin-3-ylmethyl{4-[({3-[(tert-butoxycarbonyl)amino]-6-phenylpyridin-2-yl}amino)carbonyl]benzyl}carbamate (1.5 g, 2.71 mmol) was taken up in EtOH (10.84 mL) at 0° C., evacuated and backfilled with N₂. Pd/C (0.288 g, 0.27 mmol) was added and the reaction was again purged and backfilled with N₂. Formic acid (2 mL, 53 mmol) was added and the reaction was stirred at RT and monitored by LC/MS. Reaction was complete in 2 h. The reaction was filtered through Celite and evaporated. The residue was taken up in DCM and washed with satd NaHCO₃ solution (2×50 mL). The combined organic fractions were dried over Na₂SO₄, filtered and evaporated in vacuo to provide tert-butyl(2-{[4-(aminomethyl)benzoyl]amino}-6-phenylpyridin-3-yl)carbamate. MS: cal'd 419 (MH+), exp 419 (MH+).

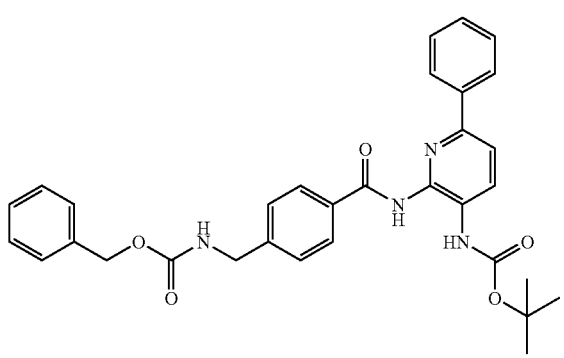 [SMILES: CC(C)(C)OC(=O)Nc1ccc(-c2ccccc2)nc1NC(=O)c1ccc(CNC(=O)OCc2ccccc2)cc1]

Benzyl{4-[({3-[(tert-butoxycarbonyl)amino]-6-phenylpyridin-2-yl}amino)carbonyl]benzyl}carbamate Benzyl chloroformate (0.06 ml, 0.420 mmol) was added to a flask containing tert-butyl(2-{[4-(aminomethyl)benzoyl]amino}-6-phenylpyridin-3-yl)carbamate (158 mg, 0.378 mmol) and DIPEA (0.15 ml, 0.859 mmol) in THF (5 mL) at 0° C. The mixture was stirred at 0° C. for 1 hour. Water was added and the products were extracted into EtOAc (2×). The combined organic extracts were washed with brine, dried over sodium sulfate and concentrated. The organic product was purified by column chromatography on silica gel Biotage 25S, eluting with EtOAc/hexanes (0%-100%) to give a pale slightly yellow transparent gel. MS: cal'd 553 (MH+), exp 553 (MH+).

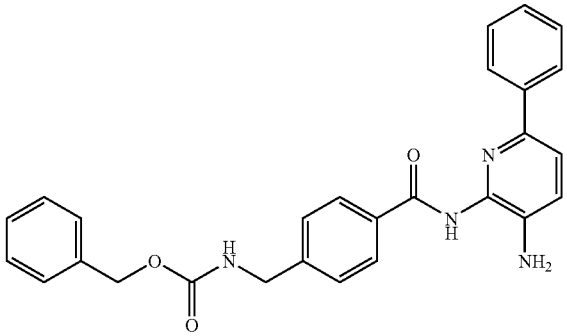

Benzyl(4-{[(3-amino-6-phenylpyridin-2-yl)amino]carbonyl}benzyl)carbamate

TFA (1 ml, 12.98 mmol) was added to a flask of benzyl{4-[({3-[(tert-butoxycarbonyl)amino]-6-phenylpyridin-2-yl}amino)carbonyl]benzyl}carbamate (70 mg, 0.127 mmol) in dichloromethane (1 ml) at room temperature and the reaction was allowed to stir for 1 hour. The reaction was quenched by the addition of saturated sodium bicarbonate until bubbling stopped. The aqueous layer was extracted (2×) with EtOAc. The combined organic fractions were dried over sodium sulfate, filtered and concentrated. The residue was then purified by reverse phase HPLC to provide the desired product. ¹H NMR (DMSO-d₆) δ: (10.36s, 1H), 7.97 (d, J=8.2 Hz, 2H), 7.90 (d, J=7.3 Hz, 3H), 7.65 (d, J=8.4 Hz, 1H), 7.08-7.41 (m, 1H), 5.12 (s, 2H), 5.02 (s, 2H), 4.26 (d, J=6.3 Hz, 2H) MS: cal'd 453 (MH+), exp 453 (MH+). The in vitro HDAC1 IC₅₀ of this compound is 32 nM. The IC₅₀ of this compound in HCT-116 cells is 590 nM. Percent Cyp inhibitions at 10 μM are 7, 25 and 24%, for Cyp3A4, 2C9, and 2D6, respectively. The inflection point for MK-499 binding is 12.2 μM.

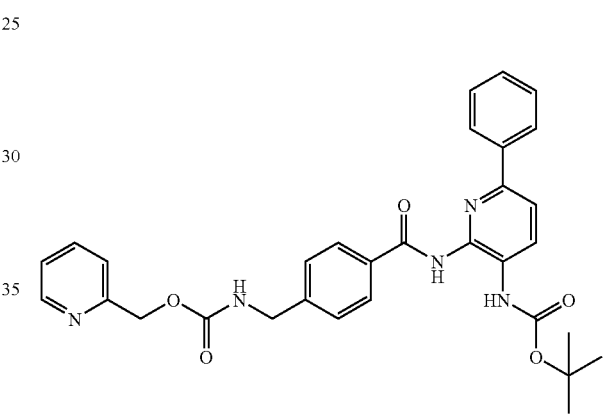

Pyridin-2-ylmethyl{4-[({3-[(tert-butoxycarbonyl)amino]-6-phenylpyridin-2-yl}amino)carbonyl]benzyl}carbamate Pyridine-2-methanol (0.0345 ml, 0.358 mmol) was added to a 0° C. cooled mixture of CDI (58.0 mg, 0.358 mmol) in THF (5 mL) and the reaction was stirred at room temperature for 1 h. Tert-butyl(2-{[4-(aminomethyl)benzoyl]amino}-6-phenylpyridin-3-yl)carbamate (150 mg, 0.358 mmol) was added to the reaction with TEA (0.050 ml, 0.358 mmol) and DBU (0.054 ml, 0.358 mmol) and the reaction stirred for 2 hours. LC/MS indicated the presence of the addition of the free amine to the CDI and thus another equivalent of pyridine-2-methanol (0.345 ml, 0.358 mmol) was added and the reaction stirred overnight. LC/MS indicated the formation of the desired product. Following evaporation of THF, water was added and the organic product was extracted (3×) with EtOAc, washed with brine and dried over sodium sulfate. The residue was purified by column chromatography on silica gel Biotage 25S, eluting with EtOAc/hexanes (0%-100%). MS: cal'd 554 (MH+), exp 554 (MH+).

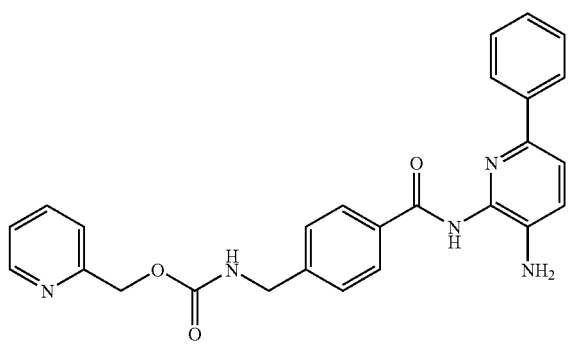

Pyridin-2-ylmethyl(4-{[(3-amino-6-phenylpyridin-2-yl)amino]carbonyl}benzyl)carbamate TFA (1 mL, 12.98 mmol) was added to a flask containing pyridin-2-ylmethyl{4-[({3-[(tert-butoxycarbonyl)amino]-6-phenylpyridin-2-yl}amino)carbonyl]benzyl}carbamate (100 mg, 0.181 mmol) in dichloromethane (2 ml) and the mixture stirred at room temperature for 1 hour. The reaction was quenched by the addition of saturated sodium bicarbonate until bubbling stopped. The aqueous layer was extracted (3×) with EtOAc and dried over sodium sulfate. The organic product was purified using HPLC. LCMS of the major UV absorbant fraction indicated the presence of the desired product. $^1$H NMR (DMSO-d$_6$) δ: 10.36 (s, 1H), 8.51 (d, J=4 Hz, 1H), 7.96-8.05 (m, 3H), 7.88-7.94 (m, 2H), 7.76-7.82 (m, 1H), 7.65 (d, J=8.3 Hz 1H), 7.32-7.45 (m, 5H), 7.18-7.32 (m, 3H), 5.12 (s, 2H), 5.09 (s, 2H), 4.28 (d, J=6.2 Hz, 2H) MS: cal'd 454 (MH+), exp 454 (MH+). The in vitro HDAC1 IC$_{50}$ of this compound is 35 nM. The IC$_{50}$ of this compound in HCT-116 cells is 560 nM. Percent Cyp inhibitions at 10 μM are 27, 47 and 24%, for Cyp3A4, 2C9, and 2D6, respectively. The inflection point for MK-499 binding is 2535 μM.

F. Compounds Synthesized According to Scheme 15

TABLE 3

| Structure | Name | MS | Salt forms | HDAC 1 IP* (nM) | Prol- 72 hr IP* (μM) |
|---|---|---|---|---|---|
| 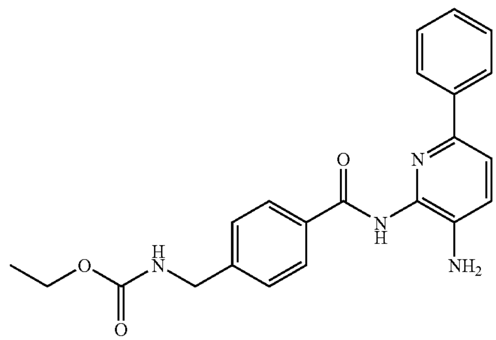 [SMILES: CCOC(=O)NCc1ccc(C(=O)Nc2nc(-c3ccccc3)ccc2N)cc1] | ethyl (4-{[(3-amino-6-phenylpyridin-2-yl)amino]carbonyl}benzyl)carbamate | cal'd 391 (MH$^+$), exp 391 (MH$^+$) | Free base | 11 | nd |
| 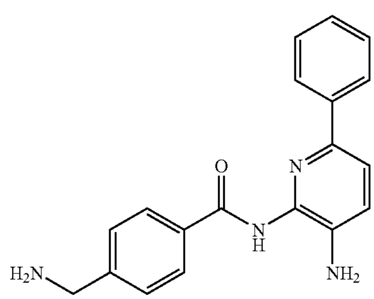 [SMILES: NCc1ccc(C(=O)Nc2nc(-c3ccccc3)ccc2N)cc1] | 4-(aminomethyl)-N-(3-amino-6-phenyl-2-pyridinyl)benzamide | cal'd 319 (MH$^+$), exp 391 (MH$^+$) | Free base | Nd | nd |
| 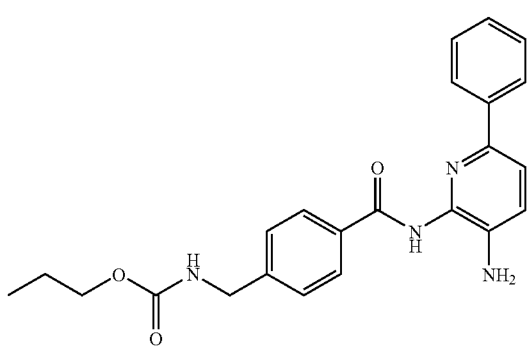 [SMILES: CCCOC(=O)NCc1ccc(C(=O)Nc2nc(-c3ccccc3)ccc2N)cc1] | propyl (4-{[(3-amino-6-phenylpyridin-2-yl)amino]carbonyl}benzyl)carbamate | cal'd 405 (MH$^+$), exp 405 (MH$^+$) | Free base | Nd | Nd |

TABLE 3-continued

| Structure | Name | MS | Salt forms | HDAC 1 IP* (nM) | Prol- 72 hr IP* (μM) |
|---|---|---|---|---|---|
| 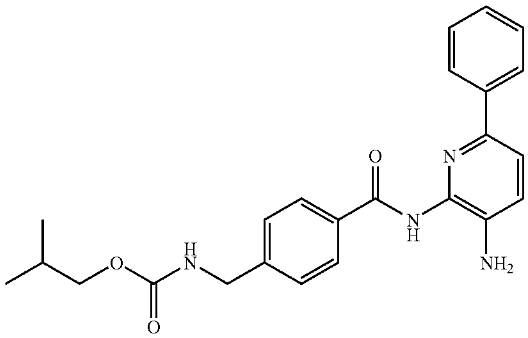 [SMILES: CC(C)COC(=O)NCc1ccc(C(=O)Nc2nc(-c3ccccc3)ccc2N)cc1] | 2-methylpropyl (4-{[(3-amino-6-phenylpyridin-2-yl)amino]carbonyl} benzyl)carbamate | cal'd 419 (MH+), exp 419 (MH+) | Free base | nd | Nd |
| 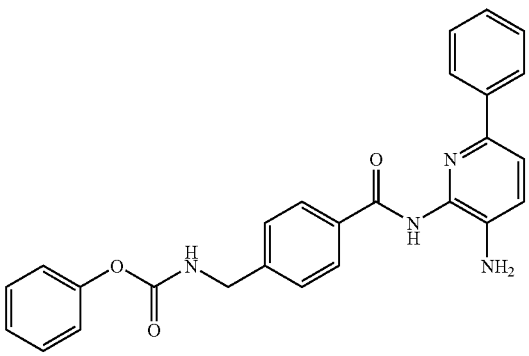 [SMILES: Nc1ccc(-c2ccccc2)nc1NC(=O)c1ccc(CNC(=O)Oc2ccccc2)cc1] | phenyl (4-{[(3-amino-6-phenylpyridin-2-yl)amino]carbonyl} benzyl)carbamate | cal'd 438 (MH+), exp 438 (MH+) | Free base | 12 | Nd |
| 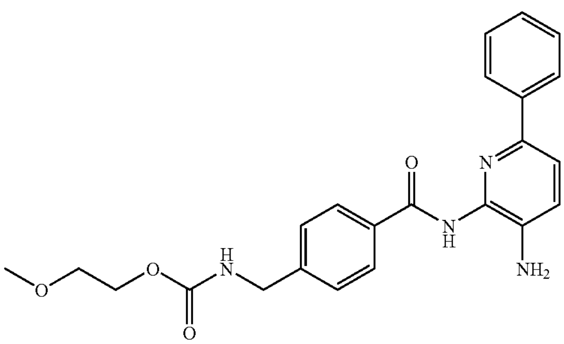 [SMILES: COCCOC(=O)NCc1ccc(C(=O)Nc2nc(-c3ccccc3)ccc2N)cc1] | 2-methoxyethyl (4-{[(3-amino-6-phenylpyridin-2-yl)amino]carbonyl} benzyl)carbamate | cal'd 421 (MH+), exp 421 (MH+) | Free base | nd | Nd |

* IP = inflection point
^ nd = not determined

G. Compounds Synthesized According to Scheme 16

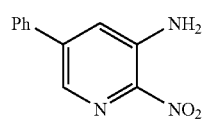

3-Amino-2-nitro-5-phenylpyridine

To 5-bromo-3-amino-2-nitropyridine (190 mg, 0.872 mmol) in a dry microwave reaction tube were added phenyl-boronic acid (159 mg, 1.31), $K_2CO_3$ (361 mg, 2.61 mmol) and $Pd(PPh_3)_4$ (101 mg, 0.087 mmol) and the reaction flask was evacuated and flushed with $N_2$ four times. To this solid reaction mixture was added anhydrous THF (2 mL) and the reaction mixture was degassed by applying vacuum and flushing with $N_2$ five times and sealed in $N_2$ atmosphere. The reaction mixture was then heated 120° C. for 2 h. After this time, LC/MS analysis of the reaction mixture should essentially show the desired product. Reaction mixture was concentrated in vacuo and to the residue was added MeOH and stirred for 30 min. All the solids were collected by filtration and washed thoroughly with MeOH and water MS: cal'd 216 (M+H)+, exp 216 (M+H)+

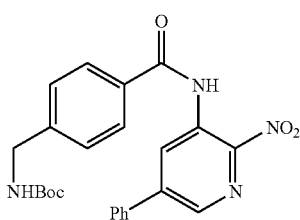

tert-Butyl(4-{[(3-nitro-6-phenylpyridin-2-yl)amino]carbonyl}benzyl)carbamate

To suspension of 4-((tert-butoxycarbonylamino)methyl)benzoic acid (42 mg, 0.167 mmol) in anhydrous THF (2 mL) was added TEA (0.047 ml, 0.335 mmol) and stirred at RT until most of the acid goes into solution. To this solution then was added isobutyl chloroformate (0.022 ml, 0.167 mmol) and the resulting suspension was stirred at RT for 30 min. After this time the reaction filtered under $N_2$ atmosphere through a sintered glass frit to give a clear solution of mixed anhydride in THF, which was then added to sodium salt of amine. To a solution of 3-amino-2-nitro-5-phenylpyridine (45 mg, 0.209 mmol) in anhydrous THF (1 mL) was cooled to −10° C. in acetone-ice bath for about 10 min. Then to this yellow solution was added a solution of NaHMDS in THF (0.210 ml, 1M) slowly drop wise. During this the reaction become dark orange red, this solution was stirred at −10° C. for 30 min. To the dark red solution of the sodium salt of amine at −10° C. was added the clear solution of mixed anhydride formed above. After the addition the reaction mixture forms a gel kind of appearance, cooling bath was removed and reaction was allowed to proceed at RT for 3 h. The reaction was quenched by addition 1N HCl (1 ml) solution in water and organic layer was separated and aqueous layer was extracted with EtOAc (2×). The combined organic layer was washed with saturated $NaHCO_3$ and brine. Finally the organic layer was dried over anhydrous $Na_2SO_4$, concentrated and residue was used in the next step without purification.

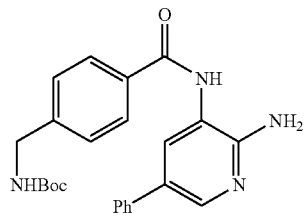 [SMILES: CC(C)(C)OC(=O)NCc1ccc(C(=O)Nc2cc(-c3ccccc3)cnc2[N+](=O)[O-])cc1]

tert-Butyl(4-{[(2-amino-5-phenylpyridin-3-yl)amino]carbonyl}benzyl)carbamate

Crude tert-butyl(4-{[(3-nitro-6-phenylpyridin-2-yl)amino]carbonyl}benzyl)carbamate was dissolved in MeOH and to it Pd on carbon was added. The reaction flask was flushed with $H_2$ and reaction was allowed to proceed under $H_2$ atmosphere over night. The crude reaction mixture was directly loaded onto column and isolated product was purified by HPLC. $^1$H NMR (600 MHz, $d_6$-DMSO) δ 9.64 (s (1H), 8.18 (d, J=2.4 Hz, 1H), 7.91 (d, J=7.8 Hz, 2H), 7.86 (d, J=2.4 Hz, 1H), 7.55 (d, J=7.2 Hz, 2H), 7.46 (t, J=6 Hz, 1H), 7.39 (m, 2H), 7.33 (d, J=7.8 Hz, 2H), 7.26 (m, 1H), 5.96 (bs, 2H), 4.16 (d, J=6 Hz, 2H), 1.37 (s, 9H).

H. Compounds that are Synthesized According to Scheme 2

TABLE 4

| Structure | Name |
|---|---|
| 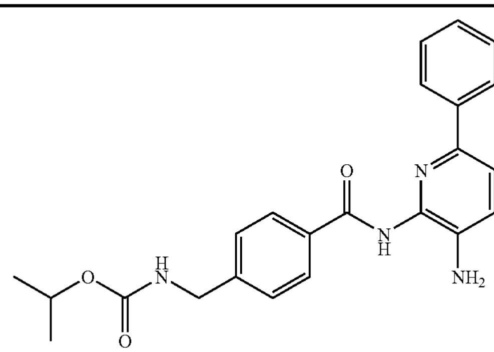 | 1-methylethyl (4-{[(3-amino-6-phenylpyridin-2-yl)amino]carbonyl}benzyl)carbamate |
|  | 4-[(acetylamino)methyl]-N-(3-amino-6-phenylpyridin-2-yl)benzamide |

TABLE 4-continued

| Structure | Name |
|---|---|
| 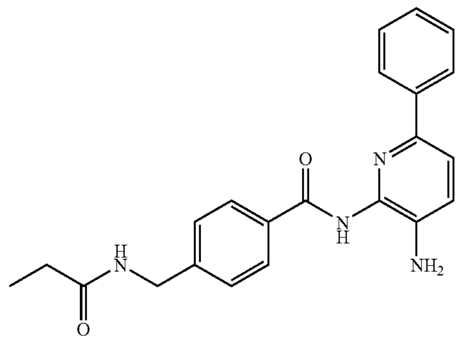 [SMILES: CCC(=O)NCc1ccc(C(=O)Nc2nc(-c3ccccc3)ccc2N)cc1] | N-(3-amino-6-phenylpyridin-2-yl)-4-[(propanoylamino)methyl]benzamide |
| 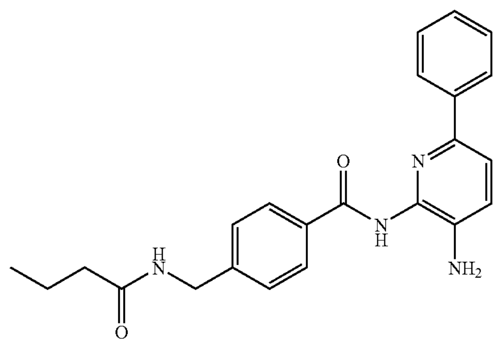 [SMILES: CCCC(=O)NCc1ccc(C(=O)Nc2nc(-c3ccccc3)ccc2N)cc1] | N-(3-amino-6-phenylpyridin-2-yl)-4-[(butanoylamino)methyl]benzamide |
| 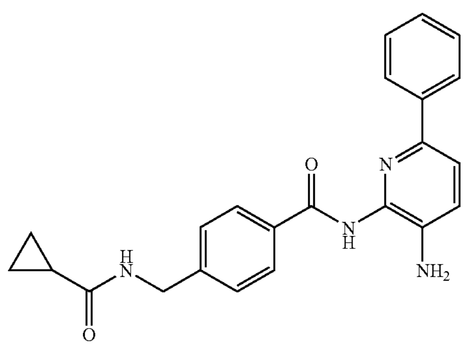 [SMILES: Nc1ccc(-c2ccccc2)nc1NC(=O)c1ccc(CNC(=O)C2CC2)cc1] | N-(3-amino-6-phenylpyridin-2-yl)-4-{[(cyclopropylcarbonyl)amino]methyl}benzamide |
| 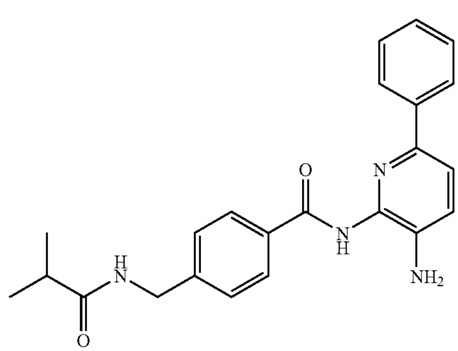 [SMILES: CC(C)C(=O)NCc1ccc(C(=O)Nc2nc(-c3ccccc3)ccc2N)cc1] | N-(3-amino-6-phenylpyridin-2-yl)-4-{[(2-methylpropanoyl)amino]methyl}benzamide |

TABLE 4-continued

| Structure | Name |
|---|---|
| 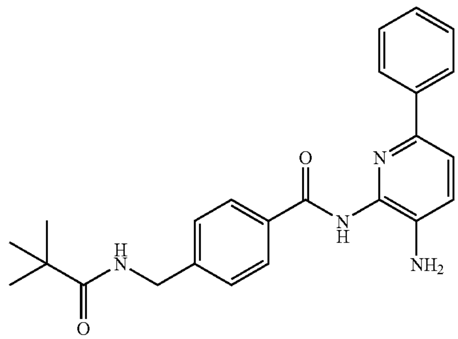 [SMILES: CC(C)(C)C(=O)NCc1ccc(C(=O)Nc2nc(-c3ccccc3)ccc2N)cc1] | N-(3-amino-6-phenylpyridin-2-yl)-4-{[(2,2-dimethylpropanoyl)amino]methyl}benzamide |
| 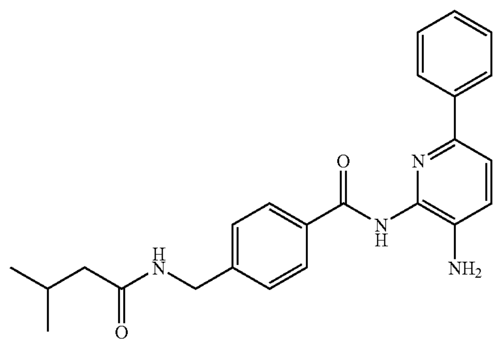 | N-(3-amino-6-phenylpyridin-2-yl)-4-{[(3-methylbutanoyl)amino]methyl}benzamide |
| 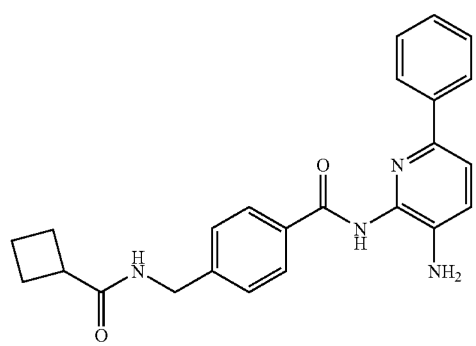 [SMILES: Nc1ccc(-c2ccccc2)nc1NC(=O)c1ccc(CNC(=O)C2CCC2)cc1] | N-(3-amino-6-phenylpyridin-2-yl)-4-{[(cyclobutylcarbonyl)amino]methyl}benzamide |
| 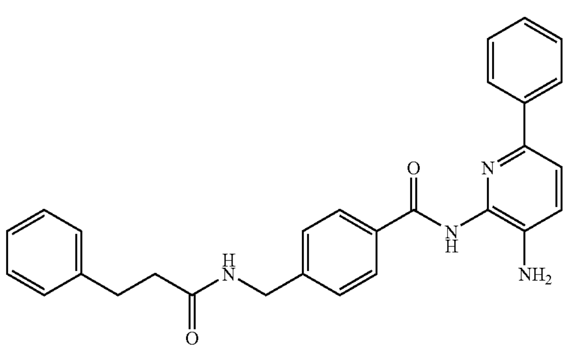 [SMILES: Nc1ccc(-c2ccccc2)nc1NC(=O)c1ccc(CNC(=O)CCc2ccccc2)cc1] | N-(3-amino-6-phenylpyridin-2-yl)-4-{[(3-phenylpropanoyl)amino]methyl}benzamide |

TABLE 4-continued

| Structure | Name |
|---|---|
| 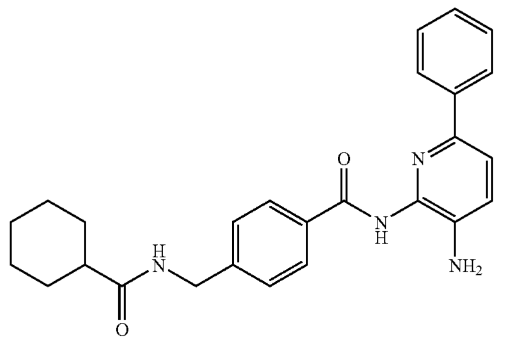 [SMILES: Nc1ccc(-c2ccccc2)nc1NC(=O)c1ccc(CNC(=O)C2CCCCC2)cc1] | N-(3-amino-6-phenylpyridin-2-yl)-4-{[(cyclohexylcarbonyl)amino]methyl}benzamide |
| 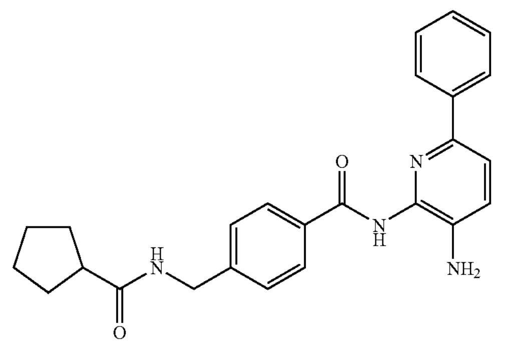 [SMILES: Nc1ccc(-c2ccccc2)nc1NC(=O)c1ccc(CNC(=O)C2CCCC2)cc1] | N-(3-amino-6-phenylpyridin-2-yl)-4-{[(cyclopentylcarbonyl)amino]methyl}benzamide |
| 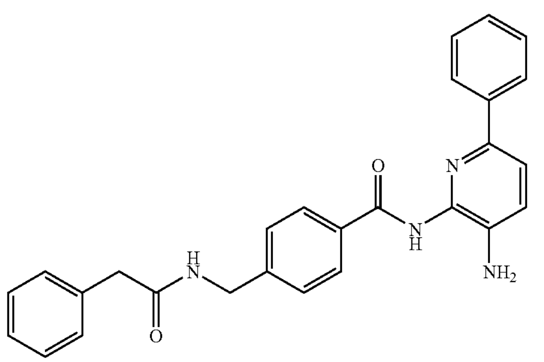 | N-(3-amino-6-phenylpyridin-2-yl)-4-{[(phenylacetyl)amino]methyl}benzamide |
| 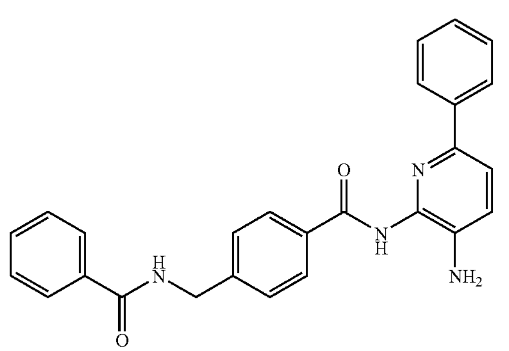 [SMILES: Nc1ccc(-c2ccccc2)nc1NC(=O)c1ccc(CNC(=O)c2ccccc2)cc1] | N-(3-amino-6-phenylpyridin-2-yl)-4-{[(phenylcarbonyl)amino]methyl}benzamide |

I. Compounds that are Synthesized According to Scheme 3

TABLE 5

| Structure | Name |
|---|---|
| 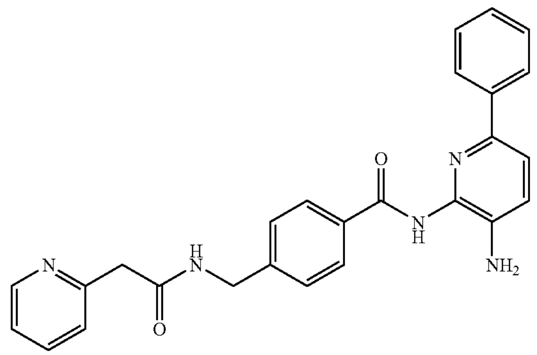 [SMILES: Nc1ccc(-c2ccccc2)nc1NC(=O)c1ccc(CNC(=O)Cc2ccccn2)cc1] | N-(3-amino-6-phenylpyridin-2-yl)-4-{[(pyridin-2-ylacetyl)amino]methyl}benzamide |
| 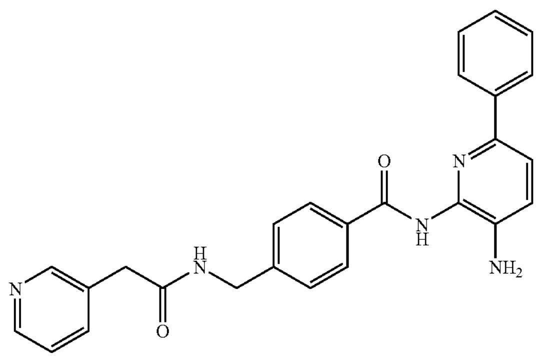 [SMILES: Nc1ccc(-c2ccccc2)nc1NC(=O)c1ccc(CNC(=O)Cc2cccnc2)cc1] | N-(3-amino-6-phenylpyridin-2-yl)-4-{[(pyridin-3-ylacetyl)amino]methyl}benzamide |
| 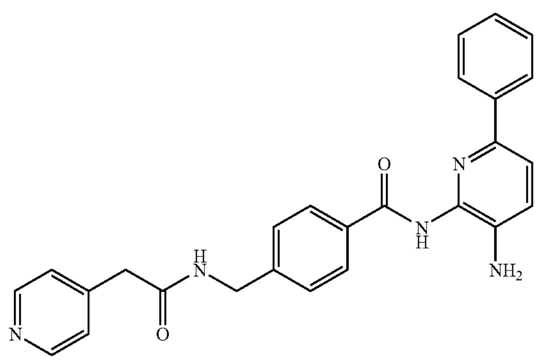 [SMILES: Nc1ccc(-c2ccccc2)nc1NC(=O)c1ccc(CNC(=O)Cc2ccncc2)cc1] | N-(3-amino-6-phenylpyridin-2-yl)-4-{[(pyridin-4-ylacetyl)amino]methyl}benzamide |
| 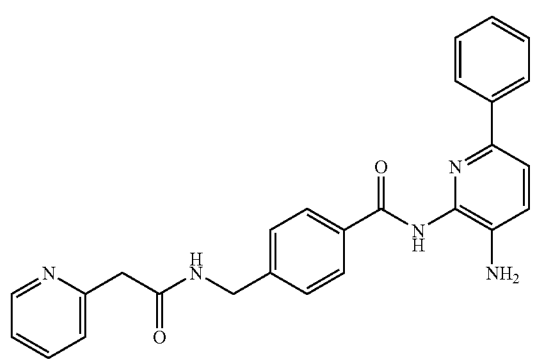 [SMILES: Nc1ccc(-c2ccccc2)nc1NC(=O)c1ccc(CNC(=O)Cc2ccccn2)cc1] | N-(3-amino-6-phenylpyridin-2-yl)-4-{[(3-pyridin-3-ylpropanoyl)amino]methyl}benzamide |

J. Compounds that are Synthesized According to Scheme 4

TABLE 6

| Structure | Name |
| --- | --- |
| 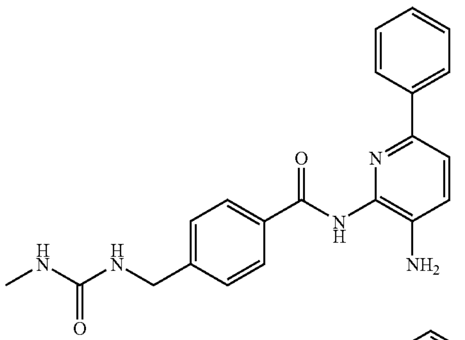 | N-(3-amino-6-phenylpyridin-2-yl)-4-({[(methylamino)carbonyl]amino}methyl)benzamide |
| 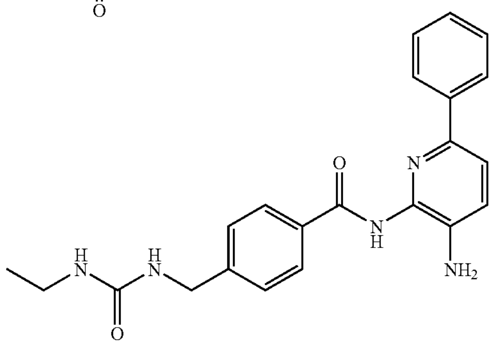 | N-(3-amino-6-phenylpyridin-2-yl)-4-({[(ethylamino)carbonyl]amino}methyl)benzamide |

K. Compounds that are Synthesized According to Scheme 12

TABLE 7

| Structure | Name |
| --- | --- |
| 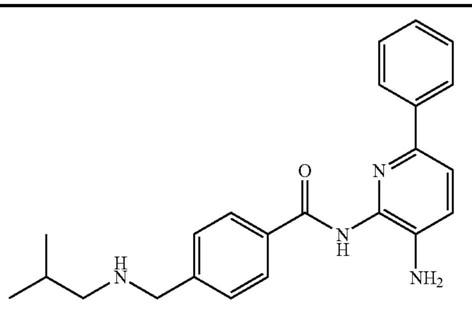 | N-(3-amino-6-phenylpyridin-2-yl)-4-[(isobutylamino)methyl]benzamide |
| 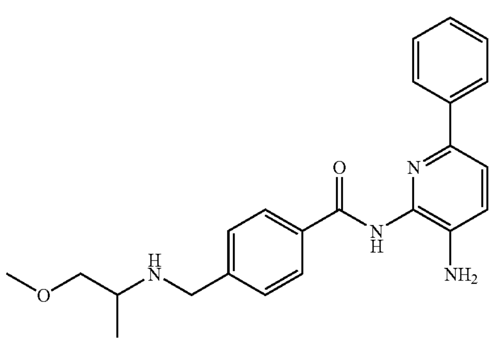 [SMILES: COCC(C)NCc1ccc(C(=O)Nc2nc(-c3ccccc3)ccc2N)cc1] | N-(3-amino-6-phenylpyridin-2-yl)-4-{[(2-methoxy-1-methylethyl)amino]methyl}benzamide |

Example 2

HDAC Inhibition by Novel Compounds
HDAC1-Flag Assay

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (BIOMOL Research Laboratories, Inc., Plymouth Meeting, Pa.). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC50) of the deacetylation reaction.

Example 3

HDAC Inhibition in Cell Lines ATP Assay

The novel compounds of the present invention were tested for their ability to inhibit proliferation of the human cervical cancer (HeLa) and colon carcinoma (HCT116) cells.

In this assay, also referred to as the ViaLight Assay, cellular ATP levels are measured as a means of quantifying cellular proliferation. This assay makes use of a bioluminescent method from Cambrex (ViaLight PLUS, cat. #LT07-121). In the presence of ATP, luciferase converts luciferin to oxyluciferin and light. The amount of light produced (emission at 565 nM) is measured and correlates with a relative amount of proliferation. Human cervical cancer (HeLa) or colon carcinoma (HCT116) cells were incubated with vehicle or increasing concentrations of compound for 48, 72 or 96 hours. Cell proliferation was quantified by adding the cell lysis reagent (provided in the Vialight assay kit) directly to culture wells, followed by addition of the ATP-monitoring reagent (containing luciferase/luciferin). The amount of light produced is then measured (emission at 565 nM). The quantity of light produced, as measured by 565 nM absorbance, is directly proportional to the number of living cells in culture.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:

1. A compound with the formula

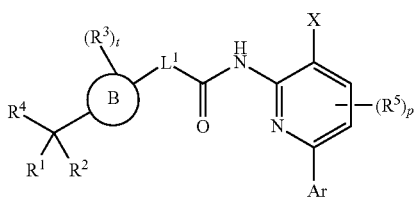

II wherein Ar is phenyl, thienyl or pyridyl, optionally substituted with halo, methyl, methoxy, amino, hydroxyl or halomethyl;

$R^1$ and $R^2$ are independently H, OH, halo, $NH_2$, $C_1$-$C_4$ alkyl, or $C_1$-$C_4$ alkoxy;

$R^3$ is independently H, OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-$NHSO_2$—, $C_1$-$C_7$ alkyl-$SO_2NH$—, $C_1$-$C_7$ alkylsulfonyl, $C_1$-$C_7$ alkylamino or di($C_1$-$C_7$)alkylamino;

$R^4$ is —$NR^6R^7$;

$R^5$ is independently H, OH, $NH_2$, nitro, CN, amide, carboxyl, $C_1$-$C_2$ alkoxy, $C_1$-$C_2$ alkyl, $C_1$-$C_2$ haloalkyl, $C_1$-$C_2$ haloalkyloxy, $C_1$-$C_2$ hydroxyalkyl, $C_1$-$C_2$ alkenyl, $C_1$-$C_2$ alkyl-C(=O)O—, $C_1$-$C_2$ alkyl-C(=O)—, $C_1$-$C_2$ alkynyl, halo, hydroxyalkoxy, $C_1$-$C_2$ alkyl-$NHSO_2$—, $C_1$-$C_2$ alkyl-$SO_2NH$—, $C_1$-$C_2$ alkylsulfonyl, $C_1$-$C_2$ alkylamino or di($C_1$-$C_2$)alkylamino;

$R^6$ is independently H, or $C_1$-$C_4$ alkyl;

$R^7$ is —$(CR^a{}_2)_sC(O)(CR^a{}_2)_qR^{13}$, or —$(CR^a{}_2)_sC(O)O(CR^a{}_2)_qR^{12}$;

$R^{12}$ is H, $C_1$-$C_4$ alkyl, $C_3$-$C_6$ cycloalkyl, heteroaryl, aryl or heterocyclic, wherein the alkyl, cycloalkyl, heteroaryl, heterocyclic or aryl is optionally substituted with aryl, heteroaryl, halo, $C_1$-$C_4$ alkyl, $N(R^6)_2$, OH, $C_1$-$C_4$ alkoxy or $C_1$-$C_4$ haloalkyl;

$R^{13}$ is H, $C_2$-$C_7$ alkyl, $C_3$-$C_6$ cycloalkyl, heteroaryl, or aryl, wherein the cycloalkyl, heteroaryl or aryl is optionally substituted with aryl, heteroaryl, halo, $C_1$-$C_4$ alkyl, $N(R^6)_2$, OH, $C_1$-$C_4$ alkoxy or $C_1$-$C_4$ haloalkyl;

$R^a$ is independently H or $C_1$-$C_4$ alkyl;

Ring B is aryl or heteroaryl;

p is 1, 2, 3 or 4;

s and q are independently 0, 1, 2, 3, or 4;

t is independently 1, 2, 3 or 4;

$L^1$ is $(CH_2)_r$, ethenyl or cyclopropyl, wherein r is 0, 1 or 2;

X is OH or $NH_2$;

or a stereoisomer or pharmaceutically acceptable salt thereof.

2. The compound of claim 1, wherein Ar is

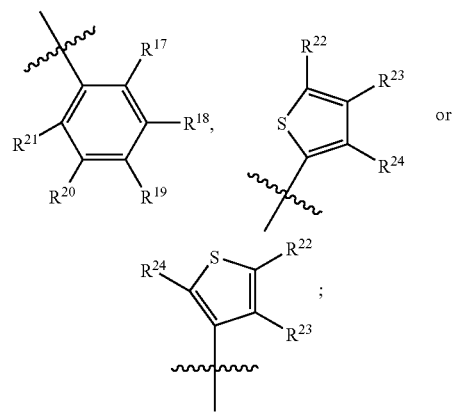

$R^1$ and $R^2$ are H;
$R^3$ is H;
$R^4$ is —$NR^6R^7$;
$R^5$ is H;
$R^6$ is H or $C_1$-$C_4$ alkyl;

$R^7$ is —C(O)O(CR$^a{}_2$)$_q$R$^{12}$;
$R^{12}$ is H, $C_1$-$C_4$ alkyl, cycloalkyl, aryl, or heteroaryl;
$R^{17}$ and $R^{21}$ are independently hydrogen or fluoro;
$R^{18}$, $R^{19}$ or $R^{20}$ are independently hydrogen, halo, methyl, methoxy or halomethyl;
$R^{22}$, $R^{23}$ and $R^{24}$ are independently hydrogen, methyl, amino, hydroxyl or halo;
$R^a$ is independently H or $C_1$-$C_4$ alkyl;
Ring B is aryl or heteroaryl;
q is independently 0, 1 or 2;
t is independently 1, 2, 3 or 4;
p is 1, 2, 3 or 4;
$L^1$ is a bond;
X is $NH_2$;
or a stereoisomer or pharmaceutically acceptable salt thereof.

3. The compound of claim 2, wherein Ar is phenyl, and all other substituents are defined in claim 2.

4. The compound of claim 2, wherein Ring B is

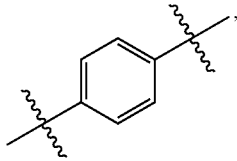 [SMILES: *c1ccc(*)cc1]

and all other substituents are defined in claim 2.

5. A compound with the formula

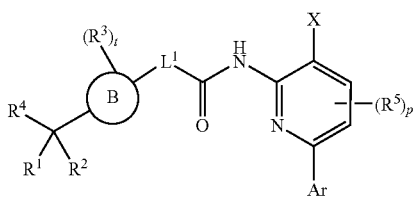

Ar is

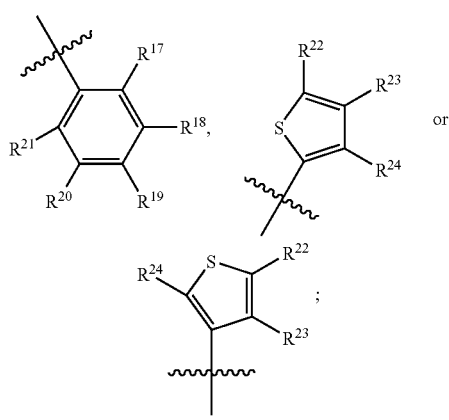

$R^1$ and $R^2$ are independently H, OH, halo, $NH_2$, $C_1$-$C_4$ alkyl, or $C_1$-$C_4$ alkoxy;
$R^3$ is H;
$R^4$ is —NR$^6$R$^7$;
$R^5$ is H;
$R^6$ is H or $C_1$-$C_4$ alkyl;

$R^7$ is —C(O)O(CR$^a{}_2$)$_q$R$^{12}$;
$R^{12}$ is aryl, or heteroaryl; wherein the aryl or heteroaryl is optionally substituted with OH, $NH_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo, hydroxyalkoxy, $C_1$-$C_7$ alkyl-NHSO$_2$—, $C_1$-$C_7$ alkyl-SO$_2$NH—, $C_1$-$C_7$ alkylsulfonyl, $C_1$-$C_7$ alkylamino or di($C_1$-$C_7$)alkylamino, aryl, heterocyclic or cycloalkyl;
$R^{17}$ and $R^{21}$ are independently hydrogen or fluoro;
$R^{18}$, $R^{19}$ or $R^{20}$ are independently hydrogen, halo, methyl, methoxy or halomethyl;
$R^{22}$, $R^{23}$ and $R^{24}$ are independently hydrogen, methyl, amino, hydroxyl or halo;
$R^a$ is independently H or $C_1$-$C_4$ alkyl;
Ring B is aryl or heteroaryl;
q is independently 0, 1 or 2;
t is independently 1, 2, 3 or 4;
p is 1, 2, 3 or 4;
$L^1$ is a bond;
X is $NH_2$;
or a stereoisomer or pharmaceutically acceptable salt thereof.

6. The compound of claim 5, wherein $R^{12}$ is phenyl or 2-pyridyl, wherein the phenyl or pyridyl is optionally substituted with OH, $NH_2$, nitro, CN, amide, carboxyl, $C_1$-$C_2$ alkoxy, $C_1$-$C_2$ alkyl, $C_1$-$C_2$ haloalkyl, $C_1$-$C_2$ haloalkyloxy, $C_1$-$C_2$ hydroxyalkyl, $C_1$-$C_2$ alkenyl, $C_1$-$C_2$ alkyl-C(=O)O—, $C_1$-$C_2$ alkyl-C(=O)—, $C_1$-$C_2$ alkynyl, halo, hydroxyalkoxy, $C_1$-$C_2$ alkyl-NHSO$_2$—, $C_1$-$C_2$ alkyl-SO$_2$NH—, $C_1$-$C_2$ alkylsulfonyl, $C_1$-$C_2$ alkylamino or di($C_1$-$C_2$)alkylamino;
q is 1 or 2;
$R^a$ is H or $C_1$-$C_2$ alkyl;
and all other substituents are as defined in claim 5.

7. The compound of claim 6, wherein $R^{12}$ is phenyl; and all other substituents are as defined in claim 6.

8. The compound of claim 6, wherein $R^{12}$ is 2-pyridyl; and all other substituents are as defined in claim 6.

9. The compound of claim 7 or 8, wherein Ar is

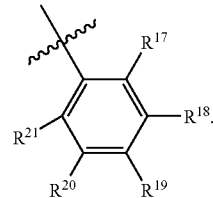

10. The compound of claim 7 or 8, wherein Ar is phenyl.

11. The compound of claim 7 or 8, wherein $R^1$ and $R^2$ are H; $R^a$ is H; $R^6$ is H, and q is 1.

12. The compound of claim 7 or 8, wherein Ring B is

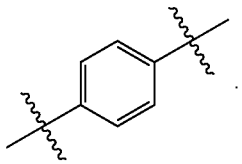 [SMILES: *c1ccc(*)cc1]

13. A compound selected from:

pyridin-3-ylmethyl{[4-({[3-amino-6-(2-thienyl)pyridin-2-yl]amino}carbonyl)phenyl]methyl}carbamate;

methyl [(4-{[(3-amino-6-phenylpyridin-2-yl)amino]carbonyl}phenyl)methyl]carbamate;

Pyridin-3-ylmethyl [(4-{[(3-amino-6-phenylpyridin-2-yl)amino]carbonyl}phenyl)methyl]carbamate;

4-(Acetylamino)-N-(3-amino-6-phenylpyridin-2-yl)benzamide;

ethyl (4-{[(3-amino-6-phenylpyridin-2-yl)amino]carbonyl}benzyl)carbamate;

1-methylethyl (4-{[(3-amino-6-phenylpyridin-2-yl)amino]carbonyl}benzyl)carbamate;

propyl (4-{[(3-amino-6-phenylpyridin-2-yl)amino]carbonyl}benzyl)carbamate;

2-methylpropyl (4-{[(3-amino-6-phenylpyridin-2-yl)amino]carbonyl}benzyl)carbamate;

phenyl (4-{[(3-amino-6-phenylpyridin-2-yl)amino]carbonyl}benzyl)carbamate;

phenylmethyl (4-{[(3-amino-6-phenylpyridin-2-yl)amino]carbonyl}benzyl)carbamate;

4-[(acetylamino)methyl]-N-(3-amino-6-phenylpyridin-2-yl1)benzamide;

N-(3-amino-6-phenylpyridin-2-yl)-4-[(propanoylamino)methyl]benzamide;

N-(3-amino-6-phenylpyridin-2-yl)-4-[(butanoylamino)methyl]benzamide;

N-(3-amino-6-phenylpyridin-2-yl)-4-{[(cyclopropylcarbonyl)amino]methyl}benzamide;

N-(3-amino-6-phenylpyridin-2-yl)-4-{[(2-methylpropanoyl)amino]methyl}benzamide;

N-(3-amino-6-phenylpyridin-2-yl)-4-{[(2,2-dimethylpropanoyl)amino]methyl}benzamide;

N-(3-amino-6-phenylpyridin-2-yl)-4-{[(3-methylbutanoyl)amino]methyl}benzamide;

N-(3-amino-6-phenylpyridin-2-yl)-4-{[(cyclobutylcarbonyl)amino]methyl}benzamide;

N-(3-amino-6-phenylpyridin-2-yl)-4-{[(3-phenylpropanoyl)amino]methyl}benzamide;

N-(3-amino-6-phenylpyridin-2-yl)-4-{[(cyclohexylcarbonyl)amino]methyl}benzamide;

N-(3-amino-6-phenylpyridin-2-yl)-4-{[(cyclopentylcarbonyl)amino]methyl}benzamide;

N-(3-amino-6-phenylpyridin-2-yl)-4-{[(phenylacetyl)amino]methyl}benzamide;

N-(3-amino-6-phenylpyridin-2-yl)-4-{[(phenylcarbonyl)amino]methyl}benzamide;

N-(3-amino-6-phenylpyridin-2-yl)-4-{[(pyridin-2-ylacetyl)amino]methyl}benzamide;

N-(3-amino-6-phenylpyridin-2-yl)-4-{[(pyridin-3-ylacetyl)amino]methyl}benzamide;

N-(3-amino-6-phenylpyridin-2-yl)-4-{[(pyridin-4-ylacetyl)amino]methyl}benzamide;

N-(3-amino-6-phenylpyridin-2-yl)-4-{[(3-pyridin-3-yl-propanoyl)amino]methyl}benzamide;

pyridin-2-ylmethyl (4-{[(3-amino-6-phenylpyridin-2-yl)amino]carbonyl}benzyl)carbamate;

N-(3-amino-6-phenylpyridin-2-yl)-4-({[(methylamino)carbonyl]amino}methyl)benzamide;

N-(3-amino-6-phenylpyridin-2-yl)-4-({[(ethylamino)carbonyl]amino}methyl)benzamide;

N-(3-amino-6-phenylpyridin-2-yl)-4-[(isobutylamino)methyl]benzamide;

N-(3-amino-6-phenylpyridin-2-yl)-4-{[(2-methoxy-1-methylethyl)amino]methyl}benzamide;

N-(3-amino-6-phenylpyridin-2-yl)benzamide;

N-(3-amino-6-phenyl-2-pyridinyl)-4-(1,1-dimethylethyl)benzamide;

benzoic acid, methyl 4-[[(3-amino-6-phenyl-2-pyridinyl)amino]carbonyl]benzoate;

4-(aminomethyl)-N-(3-amino-6-phenyl-2-pyridinyl)benzamide;

2-methoxyethyl (4-{[(3-amino-6-phenylpyridin-2-yl)amino]carbonyl}benzyl)carbamate;

tert-Butyl (4-{[(3-amino-6-phenylpyridin-2-yl)amino]carbonyl}benzyl)carbamate; and tert-Butyl (4-{[(2-amino-5-phenylpyridin-3-yl)amino]carbonyl}benzyl)carbamate;

or a stereoisomer or pharmaceutically acceptable salt thereof.

14. A pharmaceutical composition comprising a pharmaceutically effective amount of the compound according to claim 1, and a pharmaceutically acceptable carrier.

15. The compound of claim 1 that is:

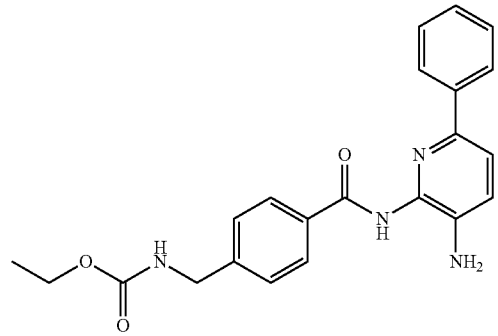

or a stereoisomer or a pharmaceutically acceptable salt thereof.

16. The compound of claim 1 that is

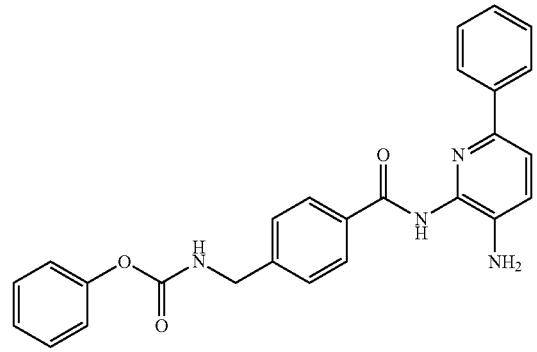 [SMILES: Nc1ccc(-c2ccccc2)nc1NC(=O)c1ccc(CNC(=O)Oc2ccccc2)cc1]

or a stereoisomer or pharmaceutically acceptable salt thereof.

17. The compound of claim 1 that is
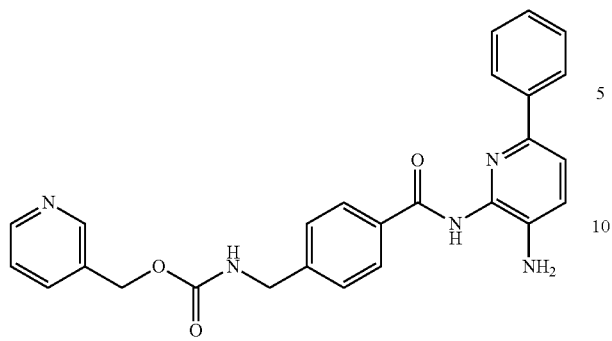
or a stereoisomer or pharmaceutically acceptable salt thereof.
18. The compound of claim 1 that is
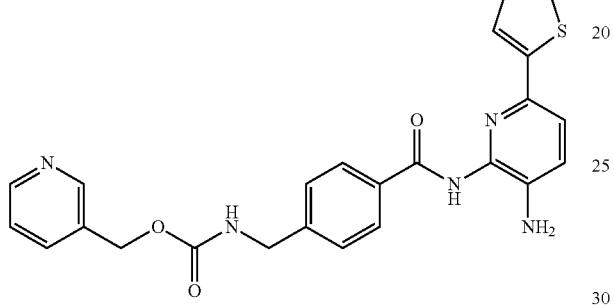
or a stereoisomer or pharmaceutically acceptable salt thereof.
19. The compound of claim 1 that is
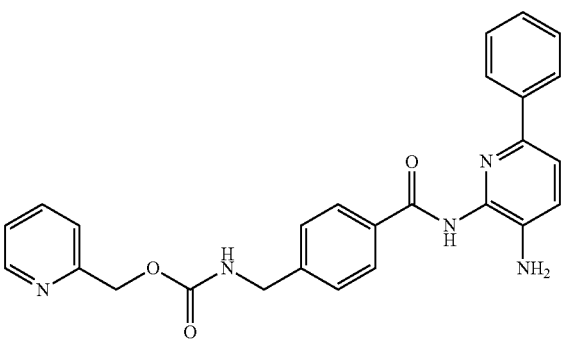 [SMILES: Nc1ccc(-c2ccccc2)nc1NC(=O)c1ccc(CNC(=O)OCc2ccccn2)cc1]
or a stereoisomer or pharmaceutically acceptable salt thereof.
* * * * *